(12) United States Patent
Kurokawa et al.

(10) Patent No.: US 6,673,569 B1
(45) Date of Patent: Jan. 6, 2004

(54) DSBA/DSBB/DSBC/DSBD EXPRESSION PLASMID

(75) Inventors: Yoichi Kurokawa, Kyoto (JP); Hideki Yanagi, Takarazuka (JP); Takashi Yura, Kyoto (JP)

(73) Assignee: HSP Research Institute, Inc., Osaka (JP)

( * ) Notice: Subject to any disclaimer, the term of this patent is extended or adjusted under 35 U.S.C. 154(b) by 0 days.

(21) Appl. No.: 09/393,171

(22) Filed: Sep. 9, 1999

(30) Foreign Application Priority Data

Sep. 9, 1998 (JP) ............................. 10-255702

(51) Int. Cl.[7] ............................... C12P 21/06
(52) U.S. Cl. .................... 435/69.1; 435/69.7; 536/23.5; 536/23.6; 536/23.7
(58) Field of Search ................ 435/69.1, 69.4, 435/69.5, 69.51, 69.52, 69.6, 70.1, 71.1, 71.2, 320.1, 455, 465; 536/23.7, 23.5, 23.6

(56) References Cited

U.S. PATENT DOCUMENTS 6,159,708 A * 12/2000 Sogo et al. ................ 435/69.1
6,197,547 B1 * 3/2001 Sogo et al. ................ 435/69.1

FOREIGN PATENT DOCUMENTS

WO    WO 9614422    5/1996

OTHER PUBLICATIONS

A Rietsch et al., Proc.Natl.Acad.Sci USA, "An in vivo pathway for disulfide bond isomerization in *Escherichia coli*," Nov. 1996, vol. 93, pp. 13048–13053.*
R Metheringham et al., Mol.Gen Genet, "Effects of mutations in genes for proteins involved in disulphide bond formation in the periplasm on the activities of anaerobically induced electron transfer chains in *Escherichia coli* K12," 1996, 253:95–102.*
D Missiakas et al., "Identification and characterization of a new disulfide isomerase–like protein (DsbD) in *Escherichia coli*," pp. 3415–3424.*
Dominique Missiakas et al., EMBO Journal, vol. 14, No. 14, pp. 3415–3424 (1995).
Satoshi Kishigami et al., Genes to Cells, vol. 1, pp. 201–208 (1996).
R. Metheringham et al., Molecular and General Genetics, vol. 253, No. 1–2, pp. 95–102 (1996).
J.C. Bardwell, Mol. Microbiol. 14(2),pp. 199–205 (1994).
M. Sone et al., J. Biol. Chem., 272(16),pp. 10349–10352 (1997).
A. Rietsch et al., Proc. Natl. Acad. Sci. USA, 93, pp. 13048–13053 (1996).
A. Knappik et al., Bio/Technol., 11, 77–83 (1993).
M. Wunderlich et al., J. Biol. Chem., 268(33),pp. 24547–24550 (1993).
C. Wulfing et al., J. Mol. Biol., 242, pp. 655–669 (1994).
J. C. Joly et al., Proc. Natl. Acad. Sci. USA, 95, pp. 2773–2777 (1998).
S. Kamitani et al., EMBO J., 11(1), pp. 57–62 (1992).
S. Kishigami et al., Genes to Cells, 1, pp. 201–208 (1996).
Y. Kohara et al., Cell, 50, pp. 495–508 (1987).
J. Perez et al., Gene, 158, pp. 141–142 (1995).
D. Koshland et al., Cell, 20, pp. 749–760 (1980).

* cited by examiner

*Primary Examiner*—Deborah Crouch
*Assistant Examiner*—Joseph Woitach
(74) *Attorney, Agent, or Firm*—Birch, Stewart, Kolasch & Birch, LLP

(57) ABSTRACT

An artificial operon comprising polynucleotides encoding each of DsbA, DsbB, DsbC and DsbD; an expression plasmid carrying the above artificial operon, usable for expression of DsbA, DsbB, DsbC and DsbD; a cotransformant harboring the above expression plasmid and an expression vector for a foreign protein; and a method for producing a foreign protein comprising culturing the cotransformant.

14 Claims, 9 Drawing Sheets

DSBA/DSBB/DSBC/DSBD EXPRESSION PLASMID

BACKGROUND OF THE INVENTION

1. Field of the Invention

The present invention relates to a DsbA/DsbB/DsbC/DsbD expression plasmid. More particularly, the present invention relates to an artificial operon comprising polynucleotides encoding each of DsbA, DsbB, DsbC and DsbD, the operon being capable of expressing a foreign protein in a soluble form while maintaining a normal conformation, an expression plasmid carrying the operon, a cotransformant harboring the expression plasmid and an expression vector for a foreign protein as well as a method for producing a foreign protein comprising culturing the cotransformant.

2. Discussion of the Related Art

Many of the eucaryote-derived proteins have disulfide bonds, and they are not usually expected to have a natural tertiary structure when expressed in the cytoplasm of E. coli under strong reductive conditions. Therefore, in the production of such a protein, it is considered to be effective to perform secretory expression into the periplasm under oxidative conditions suitable for disulfide bond formation. In addition to a strong possibility of expressing a protein having its natural conformation, there can be expected various advantages by expression via secretion, including a possibility of expressing a protein which is toxic to cells; a possibility of expressing a protein in which methionine is not added at its N-terminal; and facilitation in purification owing to a reduced amount of contaminant proteins. However, various reports on attempts on secretion of heterologous proteins into the periplasm of E. coli have been made, but not all heterologous proteins can be expressed in the forms exhibiting their activities. This is especially a problem in a case of a protein having a large number of disulfide bonds.

On the other hand, in E. coli, there have been deduced the roles of DsbA, DsbB, DsbC and DsbD which are the Dsb family proteins involved in the formation of disulfide bonds by means of biochemical tests and complementary tests using their respective deletion strains [Bardwell, J. C., Mol. Microbiol. 14, 199–205 (1994); Sone, M. et al., J. Biol. Chem., 272, 10349–10352 (1997); Rietsch, A. et al., Proc. Natl. Acad. Sci. USA, 93, 13048–13053 (1996)].

First, DsbA acts to form disulfide bonds in a nascent polypeptide chain which has been transferred into the periplasm. The disulfide bonds formed at this stage are not necessarily proper, and are then corrected into proper disulfide bonds by means of cleavage of the disulfide bonds followed by re-crosslinking by the action of DsbC. Each of DsbA and DsbC has a thioredoxin-like active site motif (Cys-X-X-Cys). In the Cys-X-X-Cys motif, 2 Cys residues are considered to participate in the reaction. In the process of the disulfide bond formation, the 2 Cys residues in the active center of DsbA oxidize a substrate peptide chain, while they themselves are reduced. Two Cys residues in the active center of DsbC are cleaved as a result of the reduction of the disulfide bonds of the substrate once formed, while they themselves are oxidized. Since a reduced form of DsbA and an oxidized form of DsbC no longer have catalytic activities, a factor for re-activating these DsbA and DsbC is necessitated. Intracellular membrane protein DsbB re-oxidizes DsbA, and intracellular membrane protein DsbD re-reduces DsbC, respectively, by action of the thioredoxin-like motifs existing in the periplasmic side.

For the purpose of improving secretion of a desired protein into the periplasm, several attempts have been made to overexpress DsbA or DsbC together with a desired protein, which could not so far be said to be successful. For example, Knappik et al. disclose that DsbA is required for the folding of an expressed product in the secretion of an antibody fragment; however, there has yet remained to be a problem that the efficiency of the folding does not change even when overexpressed [Knappik, A. et al., Bio/Technol., 11, 77–83 (1993)]. In addition, Wunderlich and Glockschuber disclose that the folding of an α-amylase/trypsin inhibitor is not improved by the overexpression of DsbA, but increased to 14 times in the presence of a reductive form of glutathione [Wunderlich, M. and Glockschuber, R., J. Biol. Chem., 268, 24547–24550 (1993)]. Further, Wulfing and Pluckthum disclose that the overexpression of DsbA exhibits some effects on the expression in soluble form of a T cell receptor fragment in the periplasm; however, it is necessary to overexpress simultaneously a heat shock sigma factor $\sigma^{32}$ in addition to DsbA [Wulfing, C. and Pluckthum, A., J. Mol. Biol., 242, 655–669 (1994)]. More recently, Joly et al. have found that the overexpression of DsbA or DsbC serves to doubly increase the expression level of an insulin-like growth factor I (IGF-I) in the periplasm; however, there remains the disadvantage that a soluble expression product is reduced contrary to expectations [Joly, J. C. et al., Proc. Natl. Acad. Sci. USA, 95, 2773–2777 (1998)].

An object of the present invention is to provide an artificial operon comprising polynucleotides encoding each of DsbA, DsbB, DsbC and DsbD, the operon being capable of expressing a foreign protein in a soluble form while maintaining a normal tertiary structure.

In one embodiment, the present invention provides an expression plasmid carrying the operon.

In another embodiment, the present invention provides a cotransformant harboring the plasmid and an expression vector for a foreign protein.

In still another embodiment, the present invention provides a method for producing a foreign protein comprising culturing the cotransformant.

These and other objects of the present invention will be apparent from the following description.

SUMMARY OF THE INVENTION

One of the subject matter of the present invention is in the findings that an accurate disulfide bond formation in the periplasm can be surprisingly efficiently carried out, and a soluble expression product can be further efficiently obtained when an expression vector of the Dsb family proteins comprising a protein (DsbA or DsbC) for forming or isomerizing disulfide bonds, as well as a protein (DsbB or DsbD) which can control the reactivity of DsbA or DsbC is constructed and the coexpression effects of these proteins in the secretion of a foreign protein are studied.

In sum, the present invention pertains to the following:

[1] an artificial operon comprising polynucleotides encoding each of DsbA, DsbB, DsbC and DsbD;

[2] an expression plasmid carrying the artificial operon according to item [1] above, usable for expression of DsbA, DsbB, DsbC and DsbD;

[3] a cotransformant harboring the expression plasmid according to item [1] above and an expression vector for a foreign protein; and

[4] a method for producing a foreign protein comprising culturing the cotransformant according to item [3] above.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

Figure 1:
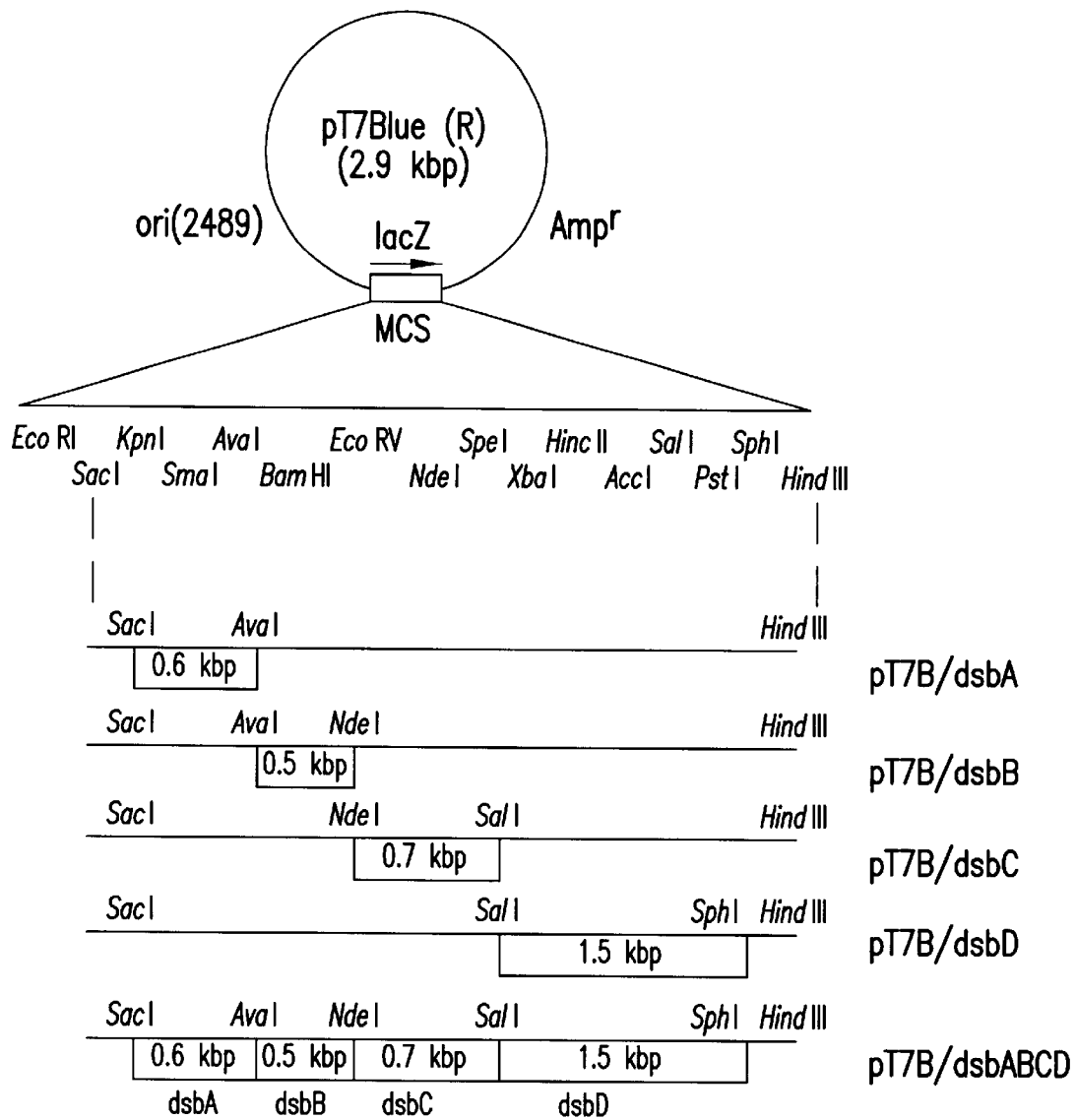
FIG. 1 is a schematic view showing pT7B/dsbA, pT7B/dsbB, pT7B/dsbC, pT7B/dsbD and pT7B/dsbABCD.

One of the significant features of the artificial operon of the present invention resides in that the artificial operon comprises genes encoding each of DsbA, DsbB, DsbC and DsbD, which are Dsb family proteins. Since the artificial operon comprises the above genes, there can be exhibited excellent effects that the disulfide bonds of a foreign protein can be properly formed when coexpressed with the foreign protein, whereby a soluble expression product can be efficiently obtained.

In the present invention, the Dsb family proteins are ones involved in the formation of disulfide bonds, and the Dsb family proteins include DsbA, DsbB, DsbC and DsbD. It is considered that the DsbA has a function for forming disulfide bonds in a nascent polypeptide chain which has been transferred into the periplasm, and the DsbC has a function for correcting the disulfide bonds formed already by DsbA into proper disulfide bonds by means of cleavage of the disulfide bonds followed by re-crosslinking. In addition, it is considered that DsbB serves to re-oxidize DsbA, and DsbD serves to re-reduce DsbC, respectively. The dsbA, dsbB, dsbC and dsbD genes encoding each of the Dsb family proteins do not form any operons, so that each of their expression is considered to be regulated independently.

The Dsb family proteins described above include a protein derived from *E. coil*, and their origins are not particularly limited as long as they have the equivalent functions mentioned above. Examples thereof include *Salmonella typhimurium, Pseudomonas aeruginosa, Haemophilus influenzae* and the like. From the viewpoint of expressing a foreign protein in a stabilized and soluble form in *E. coli*, the Dsb family proteins derived from *E. coli* are preferred.

The amino acid sequences of DsbA, DsbB, DsbC and DsbD are as shown in SEQ ID NOs: 1, 3, 5 and 7 in the Sequence Listing, respectively, and the nucleotide sequences of the genes encoding DsbA, DsbB, DsbC and DsbD are as shown in SEQ ID NOs: 2, 4, 6 and 8 in the Sequence Listing, respectively.

The amino acid sequences of DsbA, DsbB, DsbC and DsbD mentioned above may further be a sequence in which a mutation such as substitution, deletion, addition or insertion of one or more amino acid residues is introduced into each of the amino acid sequences, as long as the resulting polypeptide has an equivalent function as above. In addition, two or more kinds of mutations may be introduced in a sequence so long as the resulting polypeptide has the equivalent functions as above. The above mutations can be naturally-occurring or artificially-introduced mutations.

The nucleotide sequences of the dsbA, dsbB, dsbC and dsbD genes may also be a sequence in which a mutation such as substitution, deletion, addition or insertion of one or more bases is introduced into each of the nucleotide sequences, as long as the nucleotide sequence is encoded by the polypeptide having an equivalent function as above. In addition, two or more kinds of mutations may be introduced in a sequence so long as the nucleotide sequence has the equivalent functions as above. In addition, the nucleotide sequence may also be a nucleotide sequence consisting of genes hybridizing to any of genes as shown in SEQ ID NOs: 2, 4, 6 and 8 in the Sequence Listing under stringent conditions, as long as the nucleotide sequence is encoded by the polypeptide having an equivalent function as above. Here, the hybridization conditions are, for instance, those described in *Molecular Cloning: A Laboratory Manual*, Second Ed. (Sambrook, J. et al., published by Cold Spring Harbor Laboratory Press, New York, published 1989), and the like.

The genes described above can be obtained by means of genetic engineering techniques described in *Molecular Cloning: A Laboratory Manual*, Second Ed. mentioned above, and the like.

Concretely, the gene described above can be obtained by means of, for example, a screening method using a probe hybridizing to the gene described above; a method comprising cleaving a fragment containing a desired gene with an appropriate restriction enzyme, and cloning the fragment; PCR method using a primer pair having a sequence capable of amplifying each of the genes, and the like.

The method for obtaining the gene by PCR methods using a primer pair having a sequence capable of amplifying each gene will be described hereinbelow.

The primer used in PCR includes a primer having a sequence capable of hybridizing under stringent conditions to the nucleotide sequence of the genes described above or to a sequence complementary thereto. In the primer described above, its nucleotide sequence may have a restriction enzyme recognition site in order to facilitate the operability. Primers for amplifying dsbA gene are, for example, the primers as shown in SEQ ID NOs: 9 and 10 in the Sequence Listing. Primers for amplifying dsbB gene are, for example, the primers as shown in SEQ ID NOs: 11 and 12 in the Sequence Listing. Primers for amplifying dsbC gene are, for example, the primers as shown in SEQ ID NOs: 13 and 14 in the Sequence Listing. Primers for amplifying dsbD gene are, for example, the primers as shown in SEQ ID NOs: 15 and 16 in the Sequence Listing.

The template used for cloning by PCR methods includes, for instance, pSK220 carrying dsbA and dsbB genes [Kamitani, S. et al., *EMBO J.*, 11, 57–62 (1992)]; pSS51 carrying dsbA and dsbB genes [Kishigami, S. and Ito, K., *Genes Cells*, I, 201–208 (1996)]; Kohara Clone Nos. 468 and 648 carrying dsbC and dsbD genes [Kohara, Y. et al., *Cell*, 50, 495–508 (1987)], and the like.

The composition for a reaction mixture, thermocycle for reaction, and the like when carrying out the PCR method can be appropriately set by observing the presence or absence of the resulting amplified product. Concretely, in the amplification of, for instance, dsbA, dsbB or dsbC gene, 25 cycles of reaction can be carried out, wherein one cycle consists of 98° C. for 5 seconds, 65° C. for 2 seconds, and 74° C. for 30 seconds, by using 50 μl of a reaction mixture having the composition of 50 pmol of a primer, 10 ng of template DNA, 1 U of KOD DNA polymerase (manufactured by TOYOBO CO., LTD.), 0.2 mM dNTP, 6 mM $(NH_4)_2SO_4$, 1 mM KCl, 0.1% TRITON X-100, 0.001% BSA, 1 mM $MgCl_2$ and 120 mM Tris-HCl (pH 8.0). In addition, in the amplification of dsbD gene, 25 cycles of reaction can be carried out after treatment at 94° C. for 1 minute, wherein one cycle consists of 98° C. for 20 seconds and 68° C. for 3 minutes by using TAKARA LA TAQ™ (manufactured by Takara Shuzo Co., Ltd.) in place of the KOD DNA polymerase in the above PCR conditions, and further using a total volume of 50 μl of a reaction mixture [composition: 10 pmol of a primer, 2.5 ng of template DNA, 2.5 U of TAKARA LA TAQ™, 0.4 mM dNTP, and x10 TAKARA LA Buffer (pH 8.0)].

In the operon of the present invention, the order of the dsbA, dsbB, dsbC and dsbD genes are not particularly limited as long as the Dsb family proteins are expressed. An example includes a polycistronic operon in which the genes are arranged in tandem in the order of dsbA-dsbB-dsbC-dsbD, and the like. Incidentally, the nucleotide sequence of the polycistronic operon in which genes are arranged in tandem in the order of dsbA-dsbB-dsbC-dsbD mentioned above is as shown in SEQ ID NO: 17 in the Sequence Listing.

In addition, it is preferable that each of the dsbA, dsbB, dsbC and dsbD genes has a ribosomal binding site (SD sequence) in the upstream of its respective structural gene, and it is more preferable that each of these genes has a ribosomal binding site 7 to 10 bp upstream of its respective structural gene.

In the operon of the present invention, the genes may be present under the control of a promoter. From the viewpoint of regulation of the expression level of the Dsb family proteins, it is preferable that the promoter for controlling the transcription of the above-described operon which is present under the control of a promoter is an inducible promoter. Examples of the inducible promoter include, for instance, lac, tac, trc, trp, ara, Pzt-1, $P_L$ and T7. The lac, tac and trc promoters can be induced by using isopropyl-β-D-thiogalactopyranoside (IPTG); the trp, ara and Pzt-1 promoters can be induced by using 3-indoleacrylic acid (IAA), L-arabinose and tetracycline, respectively. The $P_L$ promoter can be induced at a high temperature (42° C.). Also usable is T7 promoter, which is specifically and strongly transcribed by T7 RNA polymerase. In a case where the T7 promoter is used, the T7 promoter can be induced with IPTG by using as a host *E. coli* strain harboring a lysogenized λ phage carrying the T7 RNA polymerase gene located downstream of the lac promoter. Among the promoters, lac, tac, trc, trp, ara, Pzt-1 and T7 are preferable from the viewpoint of facilitation in induction operability. The above promoter is contained in a known vector, and can be used by appropriately cleaving from the vector with a restriction enzyme, and the like.

In the operon of the present invention, the Dsb family proteins can be expressed more stably when the operon carries a terminator such as rrnBT1T2. These terminators are contained in a known vector, and can be used by appropriately cleaving from the vector with a restriction enzyme, or the like.

One of the significant features of the expression plasmid of the present invention resides in that DsbA, DsbB, DsbC and DsbD can be expressed by the expression plasmid, and that the expression plasmid carries the operon described above.

As described above, it is preferable that the expression plasmid of the present invention expresses the Dsb family proteins of the present invention, namely DsbA, DsbB, DsbC and DsbD under the control of an inducible promoter.

In addition, when the expression plasmid of the present invention is introduced into a host, a plasmid such as the same plasmid and the operon described above and a gene encoding a desired foreign protein may be used, or separate plasmids for carrying either one of the operon or the gene encoding a foreign protein (hereinafter referred to as coexpression plasmid) may also be used. Among them, the coexpression plasmids are preferred from the viewpoints of not necessitating to prepare a plasmid for each foreign protein as well as the stability of the plasmid in a host. The term "foreign protein" used herein refers to a desired protein except for DsbA, DsbB, DsbC and DsbD.

In order to optimize the expression level and the timing of expression of the Dsb family proteins described above without lowering the expression level of a foreign protein, it is more advantageous to independently control the expression of the Dsb family proteins from the expression of the desired protein. An inducible promoter used for expression of the Dsb family protein is preferably one different from that used in the expression of the desired protein.

When a coexpression plasmid is used as the expression plasmid described above, any plasmid can be used as long as the plasmid has a replicon compatible with an expression vector for a desired protein in *E. coli* used as a host. For example, when a vector having ColE1 replicon such as pBR322 is used as an expression vector for a desired protein, p15A replicon present in pACYC vector can be used for a plasmid used for expression of the Dsb family proteins of the present invention.

Figure 3:
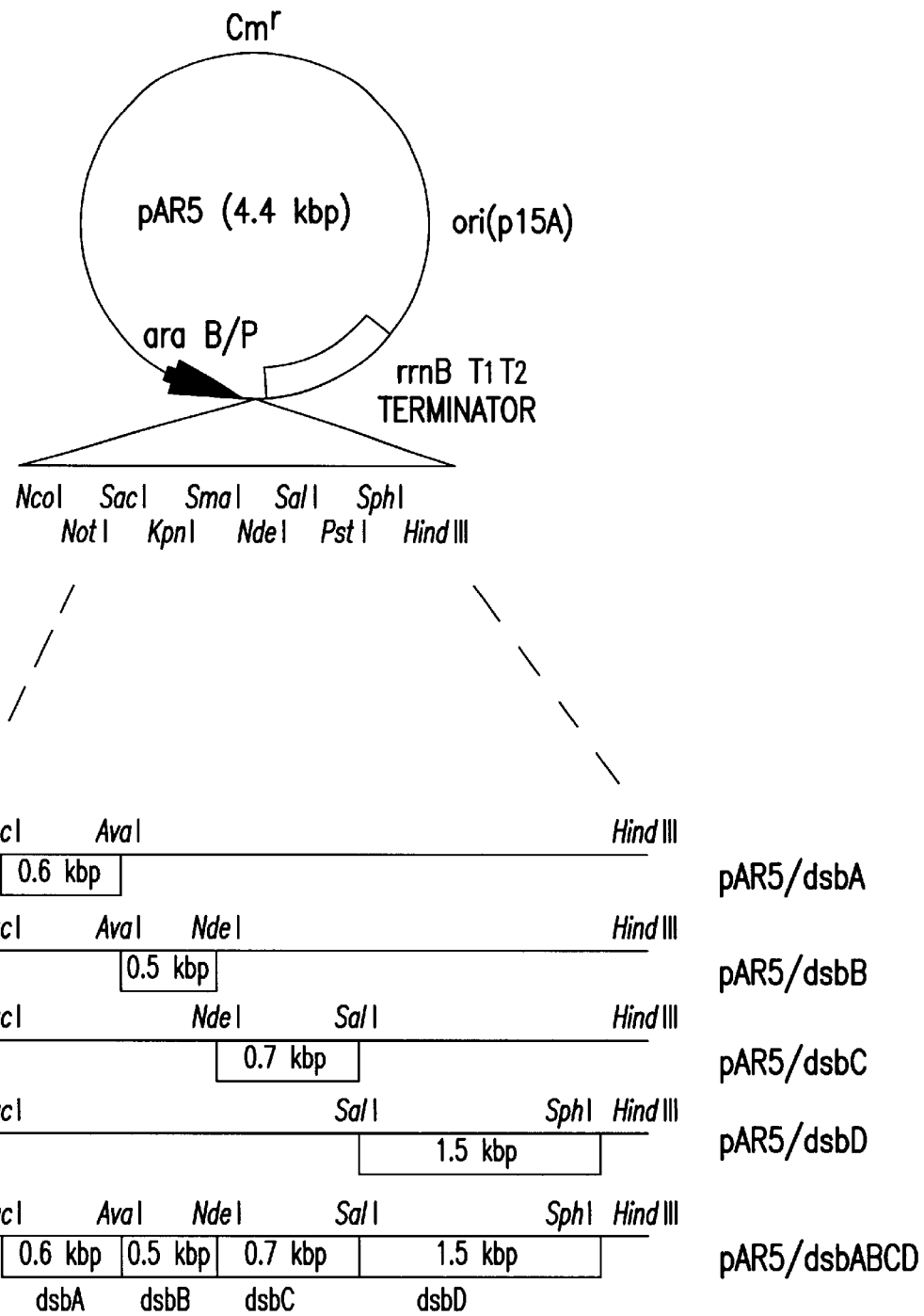
FIG. 3 is a schematic view showing an expression vector containing pAR5/dsbA, pAR5/dsbB, pAR5/dsbC, pAR5/dsbD and pAR5/dsbABCD.

Concrete examples of the expression plasmid of the present invention include a coexpression plasmid pAR5/dsbABCD. This pAR5/dsbABCD is, as shown in FIG. 3, a plasmid resulting from sequential insertions of dsbA, dsbB, dsbC and dsbD genes at the multicloning site of plasmid pAR5, wherein pAR5 carries a chloramphenicol-resistant gene and ara promoter capable of inducing expression with arabinose, which are derived from pAR3, a derivative of pACYC184 vector [Perez et al., *Gene*, 158, 141–142 (1995)], as well as the multicloning site and rrnBT1T2 terminator derived from pTrc99A (manufactured by Pharmacia) downstream of the above ara promoter. The pAR5/dsbABCD can induce the expression of the Dsb family proteins described above by adding arabinose. The pAR5/dsbABCD can also contribute to a proper disulfide bond formation in a foreign protein in the co-presence of other plasmid carrying a gene encoding the foreign protein, whereby producing a soluble expression product at a high efficiency.

The above-described plasmid can be constructed by a method, for example, described in *Molecular Cloning: A Laboratory Manual*, 2nd Ed. mentioned above.

The plasmid of the present invention may further contain a selection marker gene as occasion demands in order to facilitate selection upon transformation. Examples of such selection marker genes include ampicillin resistance (Amp$^r$) genes, kanamycin resistance (Km$^r$) genes, chloramphenicol resistance (Cm$^r$) genes, and the like. It is desired that in the coexpression plasmid, the selection marker gene is different from the selection marker gene contained in the expression vector for a foreign protein.

One of the significant features of the cotransformant of the present invention resides in that the cotransformant harbors the expression plasmid described above (coexpression plasmid) as well as an expression vector for a foreign protein.

The above cotransformant can be obtained by cotransforming an expression plasmid (the coexpression plasmid) typically exemplified by the pAR5/dsbABCD described above together with an expression vector for a foreign protein carrying a gene encoding the foreign protein.

The expression vector for a foreign gene used in the cotransformant described above is not particularly limited, and it may be a vector capable of expressing a desired foreign protein in the cytoplasm of a cell or capable of secreting a desired foreign protein into the periplasm of a cell, wherein the vector exhibits compatibility with the expression plasmid described above. Particularly preferable is a vector in which the expression of a desired foreign protein can be induced under the control of an inducible promoter. The inducible promoter includes promoters similar to those described above. The Dsb family proteins and a desired protein can separately be induced for expression by selecting a promoter other than the promoter used in the induction for expression of the Dsb family proteins in the present invention.

In addition, the expression vector for a foreign gene may also comprise a selective marker gene as occasion demands. The above selective marker gene includes those described above, and double selection of the cotransformant can be achieved by using a selective marker gene other than that contained in the expression plasmid (coexpression plasmid) of the present invention.

The expression vector for a foreign gene described above is preferably a vector capable of secreting into the periplasm of a cell, from the viewpoint of forming proper disulfide bonds in the resulting foreign protein. Examples of the vector include a vector carrying a gene encoding a polypeptide formed by adding a signal peptide of OmpA, OmpT, MalE, β-lactamase, or the like to a desired foreign protein. The above vector can be obtained, for example, by adding a polynucleotide encoding the signal peptide mentioned above by means of genetic engineering technique to a position on a gene corresponding to the N-terminal of a desired foreign protein, and incorporating the resulting gene into a known vector.

In addition, the expression vector for a foreign gene of the present invention may also contain a sequence which enables to carry out a technique for facilitating purification of a desired foreign protein, typically exemplified by, for instance, expression as a fusion protein with a protein such as β-galactosidase, glutathione-S-transferase and maltose-binding protein; expression as a protein having an added histidine tag, and the like, so long as the objects of the present invention are not hindered.

Concrete examples of host E. coli strains usable in the present invention include generally used strains, such as HB101, JM109, MC4100, MG1655 and W3110; and various mutants, including protease mutants, such as degP mutants, ompT mutants, tsp mutants, lon mutants, clpPX mutants, hslV/U mutants, lon-cLpPX double mutants and lon-clpPX-hslV/U triple mutants; plsX mutants; rpoH deletion mutants; rpoH missense mutants, and the like.

In the present invention, concrete examples of protease mutants include degP mutants, ompT mutants, tsp mutants, lon mutants, lon-clpPX double mutants and lon-clpPX-hslV/U triple mutants are preferable from the viewpoint of more stably expressing a foreign protein.

Here, a preferable lon-clpPX double mutant is E. coli strain KY2783 derived from E. coli strain W3110, prepared by introducing double deletion mutations in the lon and clpPX genes [named and identified as E. coli KY2783 and has been deposited under accession number FERM BP-6244 with the National Institute of Bioscience and Human-Technology, Agency of Industrial Science and Technology, Ministry of International Trade and Industry, of which the address is 1–3, Higashi 1-chome, Tsukuba-shi, Ibaraki-ken, 305-8566, Japan; date of original deposit: Feb. 3, 1998].

Also, the term "lon-clpPX-hslV/U triple mutant" refers to a mutant prepared by further introducing a mutation of the hslV/U gene, which encodes HslV/U protease, in the above-described lon-clpPX double mutant. A preferable lon-clpPX-hslV/U triple mutant is E. coli strain KY2893 derived from E. coli strain W3110, prepared by introducing triple deletion mutations in the lon, clpPX and hslV/U genes [named and identified as E. coli KY2893 and has been deposited under accession number FERM BP-6243 with the National Institute of Bioscience and Human-Technology, Agency of Industrial Science and Technology, Ministry of International Trade and Industry, of which the address is 1–3, Higashi 1-chome, Tsukuba-shi, Ibaraki-ken, 305-8566, Japan; date of original deposit: Feb. 3, 1998].

In the present invention, the foreign protein to be expressed may be any protein, as long as it is a foreign protein that is expressed in unstabilized form and/or insoluble form in a host, particularly in E. coli. Such foreign proteins include interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophin, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, leptin, immunoglobulins, single-chain antibodies, complement components, serum albumin, cedar pollen allergens, hypoxia-induced stress proteins, protein kinases, proto-oncogene products, transcription factors and virus-constitutive proteins.

As a method for introducing the expression plasmid of the present invention into E. coli together with an expression vector for a foreign protein, there can be employed conventional methods such as the calcium chloride method, rubidium chloride method, electroporation method and other conventional methods. The cotransformant can be screened by using chemicals in accordance with the selection marker genes. The expression of the foreign protein can, for example, be confirmed by such means as Western blotting analysis.

One of the significant features of the method for producing a foreign protein of the present invention resides in culturing the cotransformant described above. The production method can, for example, be carried out by a process comprising culturing a cotransformant under induction conditions for the Dsb family proteins suitable for stabilization and/or solubilization of a desired foreign protein to allow expression of the Dsb family proteins and the foreign protein; thereafter collecting the cells; disrupting the collected cells; and isolating and purifying the foreign protein in accordance with a purification method suitable for the foreign protein.

The induction conditions described above vary with inducible promoters used in the expression plasmid of the present invention and the expression vector for a foreign protein, and the conditions may be such that the expression levels of DsbA, DsbB, DsbC and DsbD are at levels suitable for the foreign protein to be solubilized. For example, the induction conditions can be determined as follows.

First, an inducer for the promoter described above is added with varying its concentrations and addition timings. The cells expressing a foreign protein are collected, and the collected cells are disrupted and extracted to obtain cell extracts. Each of the resulting extracts is subjected to, for instance, SDS-PAGE, and the bands ascribed to the proteins in the gel are visualized by Coomassie brilliant blue- or silver-staining. Among the visualized bands, the concentration of the band ascribed to the foreign protein is examined by, for instance, a densitometry, whereby finding appropriate induction conditions.

Since the culture conditions of the cotransformant vary with the microorganism used as a host, they are not particularly limited. The optimum conditions can be determined by examining the expression level of a foreign protein expressed under each of culturing conditions by setting various culture timing and culture temperatures, in a manner similar to the case of the determination of the induction conditions described above.

The foreign protein can be isolated and purified by any known protein purification methods, including salting-out, ion exchange chromatography, hydrophobic chromatography, affinity chromatography and gel filtration chromatography.

EXAMPLES

The present invention will be further described hereinbelow by means of the following Examples, and the present invention is by no means limited to these Examples.

Example 1

Cloning of Genes Encoding Dsb Family Proteins

Each of genes dsbA, dsbB, dsbC and dsbD, each of which is a structural gene respectively encoding DsbA, DsbB, DsbC and DsbD, which are Dsb family proteins, was cloned by PCR method. As the primers, those which were designed so that a ribosomal binding site should be located at 7 to 10 bp upstream in each of the structural genes were used. There were used as the primers for amplifying the dsbA gene, the primers as shown in SEQ ID NOs: 9 and 10 in the Sequence Listing; as the primers for amplifying the dsbB gene, the primers as shown in SEQ ID NOs: 11 and 12 in the Sequence Listing; as the primers for amplifying the dsbC gene, the primers as shown in SEQ ID NOs: 13 and 14 in the Sequence Listing; and as the primers for amplifying the dsbD gene, the primers as shown in SEQ ID NOs: 15 and 16 in the Sequence Listing. Incidentally, the primers were so designed to have restriction enzyme recognition sites as given below in the nucleotide sequences.

Primer (SEQ ID NO: 9): SacI;
Primer (SEQ ID NO: 10): AvaI;
Primer (SEQ ID NO: 11): AvaI;
Primer (SEQ ID NO: 12): NdeI;
Primer (SEQ ID NO: 13): NdeI;
Primer (SEQ ID NO: 14): SalI;
Primer (SEQ ID NO: 15): SalI; and
Primer (SEQ ID NO: 16): SphI.

As templates, there were used pSK carrying dsbA and dsbB genes [Kamitani, S. et al., *EMBO J.*, 11, 57–62 (1992)]; pSS51 [Kishigami, S. and Ito, K., *Genes Cells*, 1, 201–208 (1996)]; and Kohara Clone Nos. 468 and 648 carrying dsbC and dsbD genes [Kohara, Y. et al., *Cell*, 50, 495–508 (1987)], which were made available by Dr. Yoshinori Akiyama, The Institute of Virus Research, Kyoto University.

The PCR conditions are given hereinbelow.

There was obtained 50 µl of a reaction mixture having the composition of 50 pmol of each of primers, 10 ng of template DNA, 1 U of KOD DNA polymerase (manufactured by TOYOBO CO., LTD.), 0.2 mM dNTP, 6 mM $(NH_4)_2SO_4$, 1 mM KCl, 0.1% TRITON X-100, 0.001% BSA, 1 mM $MgCl_2$ and 120 mM Tris-HCl (pH 8.0). The resulting reaction mixture was set in GENEAMP™ PCR System 2400 (manufactured by Perkin-Elmer), and 25 cycles of reaction were carried out, wherein one cycle consisted of 98° C. for 5 seconds, 65° C. for 2 seconds, and 74° C. for 30 seconds.

As a result of carrying out PCR under the conditions described above, when pSK220 and pSS51 carrying dsbA and dsbB genes were used as templates, there was found specific amplification of about 0.6 kb and about 0.5 kb fragments which have been considered to be corresponding to dsbA and dsbb genes, respectively. On the other hand, when Kohara Clone No. 468 carrying dsbC gene was used as a template, there was found specific amplification of a fragment of about 0.7 kb which has been considered to be corresponding to dsbC gene. Alternatively, when Kohara Clone No. 648 carrying dsbD gene was used as a template, there was found to be no amplification of the fragment corresponding to dsbD gene.

Therefore, in order to clone the dsbD gene, after treatment at 94° C. for 1 minute, 25 cycles of reaction can be carried out wherein one cycle consisted of 98° C. for 20 seconds and 68° C. for 3 minutes by using TaKaRa LA Taq™ (manufactured by Takara Shuzo Co., Ltd.) in place of the KOD DNA polymerase in the above PCR conditions, and further using a total volume of 50 µl of a reaction mixture [composition: 10 pmol of each of primers, 2.5 ng of template DNA, 2.5 U of TaKaRa LA Taq™, 0.4 mM dNTPs, and ×10 TaKaRa LA Buffer (pH 8.0)]. As a template, Kohara Clone No. 648 was used. As a result, there was found an amplification of about 1.5 kb fragment, which is considered to correspond to the dsbD gene.

The nucleotide sequence of the amplified fragment thus obtained was determined, and as a result, it was elucidated that each of genes dsbA, dsbB, dsbC and dsbD was obtained. The nucleotide sequences of dsbA, dsbB, dsbC and dsbD are as shown in SEQ ID NOs: 2, 4, 6 and 8 in the Sequence Listing, respectively.

Subsequently, each of the amplified fragments obtained as described above was ligated to the multicloning site of pT7Blue(R) (manufactured by Novagen), whereby constructing each of the plasmids resulting from singly ligating any one of dsbA, dsbB, dsbC or dsbD to pT7Blue(R) (each plasmid being referred to as pT7B/dsbA, pT7B/dsbB, pT7B/dsbC and pT7B/dsbD, respectively); as well as a plasmid resulting from ligating to pT7Blue(R) an operon (SEQ ID NO: 17) obtained by tandemly connecting dsbA, dsbB, dsbC and dsbD (hereinafter referred to as "pT7B/dsbABCD"). Each of the plasmids is shown in FIG. 1.

Example 2

Construction of Expression Vector

Figure 2:
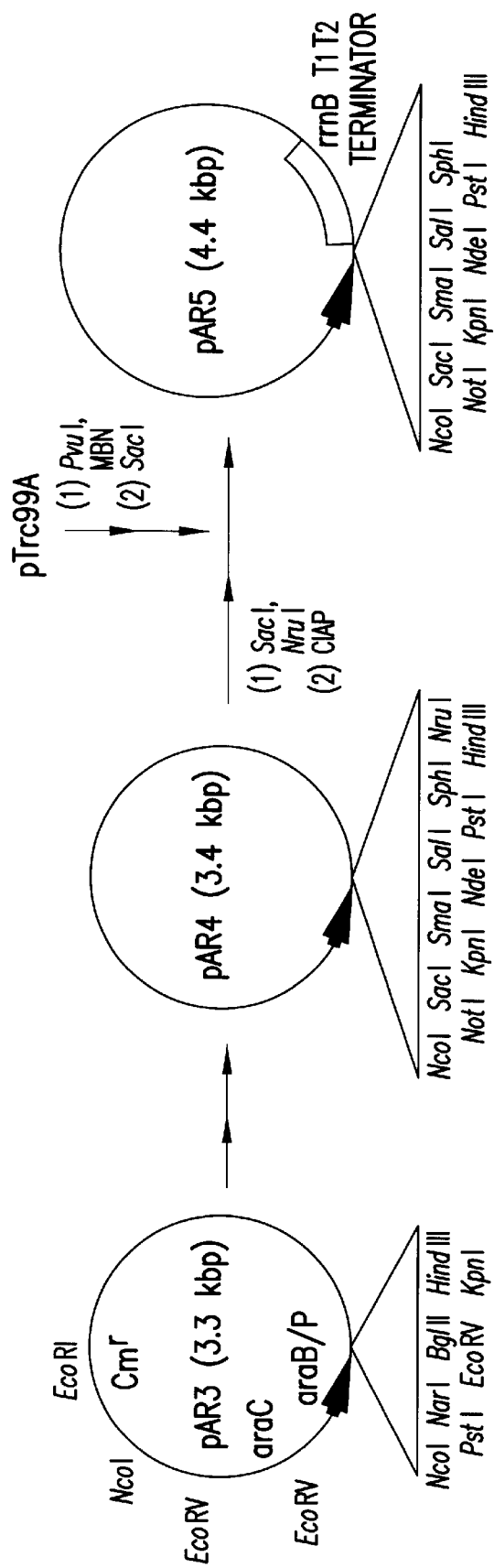
FIG. 2 is a schematic view showing the construction of an expression vector.

It is considered that the 4 genes (dsbA, dsbB, dsbC and dsbD) encoding the Dsb family proteins do not form an operon, and expression of each gene is regulated independently. Accordingly, there was constructed an expression vector in which the 4 genes form a polycistronic operon, and expression of these genes is inducible by adding arabinose. FIG. 2 shows the strategy of construction.

In order that the structural genes for the Dsb family proteins can be expressed independently from a structural gene for a model protein, the synthetic DNA (SEQ ID NO: 18) having a recognition sequence of various restriction enzymes was ligated to the PstI-HindIII site of pAR3, wherein pAR3 [chloramphenicol-resistant and capable of inducing and expressing with arabinose] was derived from pACYC184, which was constructed by Perez et al. [see Gene, 158, 141–142 (1995)], to give pAR4 having a multicloning site.

Subsequently, a fragment comprising rrnBT1T2 terminator was cut out by treating pTrc99A (manufactured by Pharmacia) with PvuI, blunt-ending the resulting fragment with Mung Bean Nuclease, and thereafter treating the blunt-ended fragment with SacI. The resulting fragment was ligated to the SacI-NruI sites of the above-described pAR4, to give pAR5. The pAR5 mentioned above is capable of expressing in the coexistence of a plasmid carrying ori of pBR322, so that the expression level of an expression product derived from a foreign gene inserted into the multicloning site can be regulated by adding arabinose.

Example 3

Construction of Expression Plasmids for Dsb Family Proteins and Confirmation of Expression Thereof A SacI-HindIII fragment was cut out from each of plasmids pT7Blue(R)/dsbA, pT7Blue(R)/dsbB, pT7Blue(R)/dsbC, pT7Blue(R)/dsbD and pT7Blue(R)/dsbABCD each obtained in Example 1, and then the fragment was inserted into the SacI-HindIII sites in the multicloning site of pAR5 obtained in Example 2. FIG. 3 shows the resulting expression plasmids in which any one of DsbA, DsbB, DsbC and DsbD is ligated respectively thereto (referred to as pAR5/dsbA, pAR5/dsbB, pAR5/dsbC and pAR5/dsbD, respectively), as well as the expression plasmid in which these 4 inserts are tandemly connected to form a polycistronic operon (pAR5/dsbABCD).

Expression of the Dsb family proteins was attempted by transforming *E. coli* JM109 with each of the plasmids obtained as described above. Competent cells were obtained from *E. coli* JM109 by the PEG-DMSO method and transformed with $1.0 \times 10^{-2}$ μg of any one of the above expression plasmids pAR5/dsbA, pAR5/dsbB, pAR5/dsbC, pAR5/dsbD and pAR5/dsbABCD. Screening of the transformants was carried out by using their resistivity to chloramphenicol as an index.

Subsequently, each of the resulting transformants was cultured at 37° C. in 5 ml of L medium containing 34 μg/ml chloramphenicol. Arabinose was added so as to have the final concentrations of 0, 200 and 2000 μg/ml, respectively, when Klett units reached around 20. Two hours later, each culture was sampled, and the cells contained in the resulting culture were harvested. The cells were subjected to precipitation treatment with TCA, to give whole cell protein. The whole cell protein obtained as above was subjected to SDS-PAGE analysis. The results are shown in FIG. 4.

Figure 4:
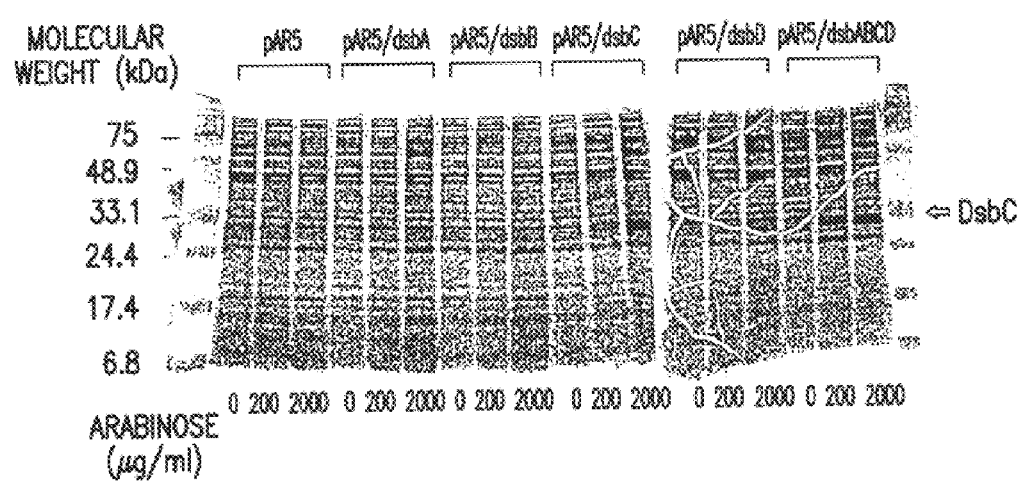
FIG. 4 shows analytic results on SDS-PAGE of the expressed Dsb family proteins.

As shown in FIG. 4, it was confirmed that when pAR5/dsbC and pAR5/dSbABCD were used, bands with a molecular weight of about 24000 which were deduced to be corresponding to DsbC, were increased significantly depending on the arabinose concentration.

Although no bands corresponding to the other Dsb products could be detected, the expression of each of the Dsb family proteins was confirmed by examining the presence or absence of the complementation of each of deletion mutation of dsbA, dsbB and dsbD. As a result, it could be confirmed that the function for each of the Dsb family proteins was complemented in each Dsb-deletion mutant.

Example 4

Construction of Expression Plasmids pTrc-OmpA and pTrc-OmpT for Secretion of Foreign Protein A plasmid resulting from insertion of a synthetic oligonucleotide (5'-terminal: blunt end; 3-terminal: NaeI and EcoRI sites) encoding the signal peptide of OmpA or OmpT as shown below into the NcoI(blunted with Mung Bean Nuclease)-EcoRI sites of the expression plasmid pTrc99A for *E. coli* was named pTrc-OmpA or pTrc-OmpT.
Oligonucleotide encoding OmpA signal sequence [Met Lys Lys Thr Ala Ile Ala Ile Ala Val Ala Leu Ala Gly Phe Ala Thr Val Ala Asn Ala (SEQ ID NO: 19)]:

5'-atgaaaaaga cagctatcgc gattgcagtg gcactggctg gtttcgctac cgtagcg-
   cag gccggctgaa ttc-3'        (SEQ ID NO: 20)

Oligonucleotide encoding OmpT signal sequence [Met Arg Ala Lys Leu Leu Gly Ile Val Leu Thr Thr Pro Ile Ala Ile Ser Ser Phe Ala (SEQ ID NO: 21)]:

5'-atgcgcgcga aactgctggg tattgtcctg acgaccccga tcgcgatcag
   ctcttttgcc ggctgaattc-3'        (SEQ ID NO: 22)

Example 5

Construction of Secretion Plasmid for NGF-β

An EcoRI-BamHI fragment of cDNA (manufactured by R&D Systems) encoding an amino acid sequence in which N-terminal signal sequence portion of human nerve growth factor-β (NGF-β) was deleted was inserted into the EcoRI-BamHI sites of pTrc-OmpT obtained in Example 4. Subsequently, the following synthetic oligonucleotide linker (blunt end-EcoRI site) corresponding to the N-terminal portion of NGF was treated with polynucleotide kinase and thereafter inserted to the NaeI-EcoRI site of the resulting plasmid, to give a secretion plasmid pTrc-OmpT/NGF for NGF-β.
NGF Linker:

5'-agcagctccc atccgatctt ccaccgcggc gaattc-3'  (SEQ ID NO: 23)

Example 6

Construction of Secretion Plasmid for HRP

The region corresponding to the structural gene was amplified by PCR method using horseradish peroxidase (HRP) cDNA (manufactured by R&D Systems) as a template. The resulting fragment was treated with BamHI and then with polynucleotide kinase, and thereafter the treated fragment was inserted into the NaeI-EcoRI sites of pTrc-OmpA, to give a secretion plasmid pTrc-OmpA/HRP for HRP. The primers used in the PCR method are as shown below. Primer:

HRP-F: 5'-atgcagttaa ccccctacatt c-3'     (SEQ ID NO: 24)

HRP-R: 5'-ggggaattcg gatccttatt a-3'     (SEQ ID NO: 25)

Example 7

Enhancement Effect of DsbABCD on Expression of Foreign Protein in Periplasm The effects of DsbABCD (influence on growth of cells, changes in the expression level and localization of the product) were examined in the cells cotransformed with the NGF-β secretion plasmid or the HRP secretion plasmid obtained in Example 5 or 6 and pAR5/dsbABCD. For each of cells grown at 37° C. in the L medium, DsbABCD was induced by adding arabinose (0 to 2000 μg/ml), and NGF-β or HRP was each induced by adding IPTG (50 μM). Each of accumulated proteins in cells were subjected to SDS-PAGE analysis and Western blotting method. The whole cell extract was obtained in the same manner as in Example 3. In addition, the periplasm soluble fraction was obtained by a method of treating the cells with lysozyme in the presence of isotonic sucrose [Koshland, D. and Botstein, D., *Cell*, 20, 749–760 (1980)].

(1) Effects on NGF Expression

When pTrc-OmpT/NGF and vector pACYC184 without inserts were coexistent, the growth of the cells was not found to be inhibited even when the arabinose concentration increased up to 200 μg/ml, but the growth of the cells tended to be inhibited at the arabinose concentration of 2000 μg/ml. On the other hand, when pTrc-OmpT/NGF and pAR5/dsbABCD were coexistent, the growth of the cells was not inhibited at all, and their growth rate increased about 10% at its maximum as the arabinose concentration increased.

Subsequently, in order to study the expression level of NGF-β in the whole cell, or the amount of NGF-β accumulated in the periplasm soluble fraction, with varying the arabinose concentration, 80 μl of sample corresponding to a culture medium with Klett units 80 of the whole cell and the periplasm soluble fraction was subjected to SDS-PAGE analysis. The results of SDS-PAGE analysis are shown in FIG. 5.

Figure 5:
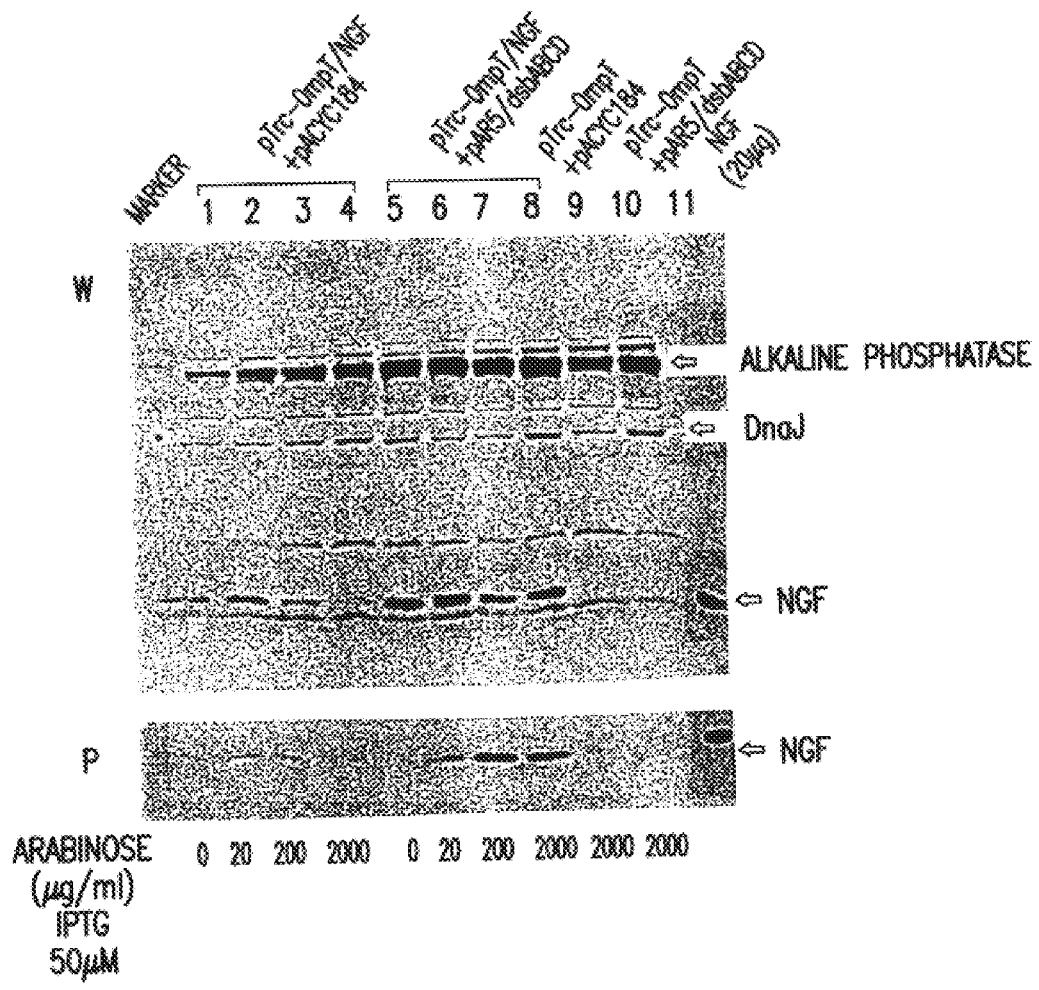
FIG. 5 shows changes in a total expression level of NGF-β or in a product level accumulated in each fraction, with respect to the change in the arabinose concentration (W: whole cell; P: periplasm)

As shown in FIG. 5, in the control where pTrc-Ompt/NGF and vector pACYC184 were coexistent, both the expression level of OmpT-NGF-β in the whole cell and in the periplasm soluble fraction were hardly changed even when the arabinose concentration was changed from 0 to 200 μg/ml, and the expression level of the product OmpT-NGF-β was significantly lowered at the arabinose concentration of 2000 μg/ml. A total expression level of OmpT-NGF-β in the coexistence of pTrc-OmpT/NGF and pAR5/dsbABCD was hardly changed (approximately 1 to 2 mg/l culture) even when the arabinose concentration was changed from 0 to 2000 μg/ml. The expression level of OmpT-NGF-β in the periplasm soluble fraction tended to be increased as the arabinose concentration was raised, so that almost all of the expressed OmpT-NGF-β were detected in the periplasm soluble fraction.

(2) Effect on HRP Expression

Figure 6:
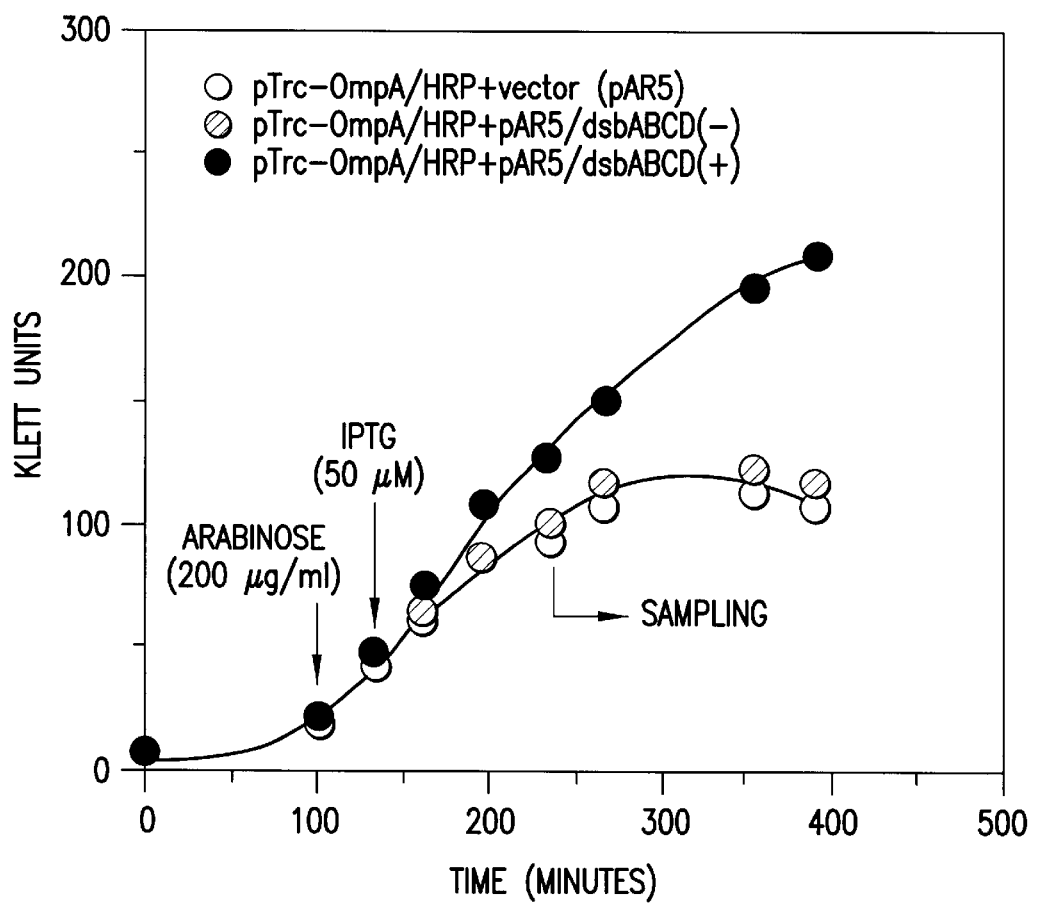
FIG. 6 is a graph showing the growth of cells in the HRP expression.

The growth of strains measured by Klett units in expression of HRP examined are shown in FIG. 6. In addition, in order to examine the expression level of HRP in the whole cell or the amount of HRP accumulated in the periplasm soluble fraction with varying concentrations of arabinose, a sample containing 60 μl culture with Klett units 80 of each of the whole cell or the periplasm soluble fraction was subjected to SDS-PAGE analysis. The results of SDS-PAGE analysis are shown in FIG. 7.

As shown in FIG. 6, in the case where pTrc-OmpA/HRP and pAR5/dsbABCD were coexistent, when arabinose was not added, growth of the cells stopped about 2 hours after adding IPTG, thereby showing significant inhibition of growth of the cells, and when arabinose was added (final concentration: 200 μg/ml), the inhibition of growth of the cells was eliminated, and the growth of the cells did not stop even at 4 hours after adding IPTG. When pTrc-OmpA/HRP and vector pAR3 without inserts were coexistent, the inhibition of growth of the cells was not ameliorated at all. These results suggest that the elimination of growth inhibition when OmpA-HRP is expressed depends on expression of DsbABCD.

Figure 7:
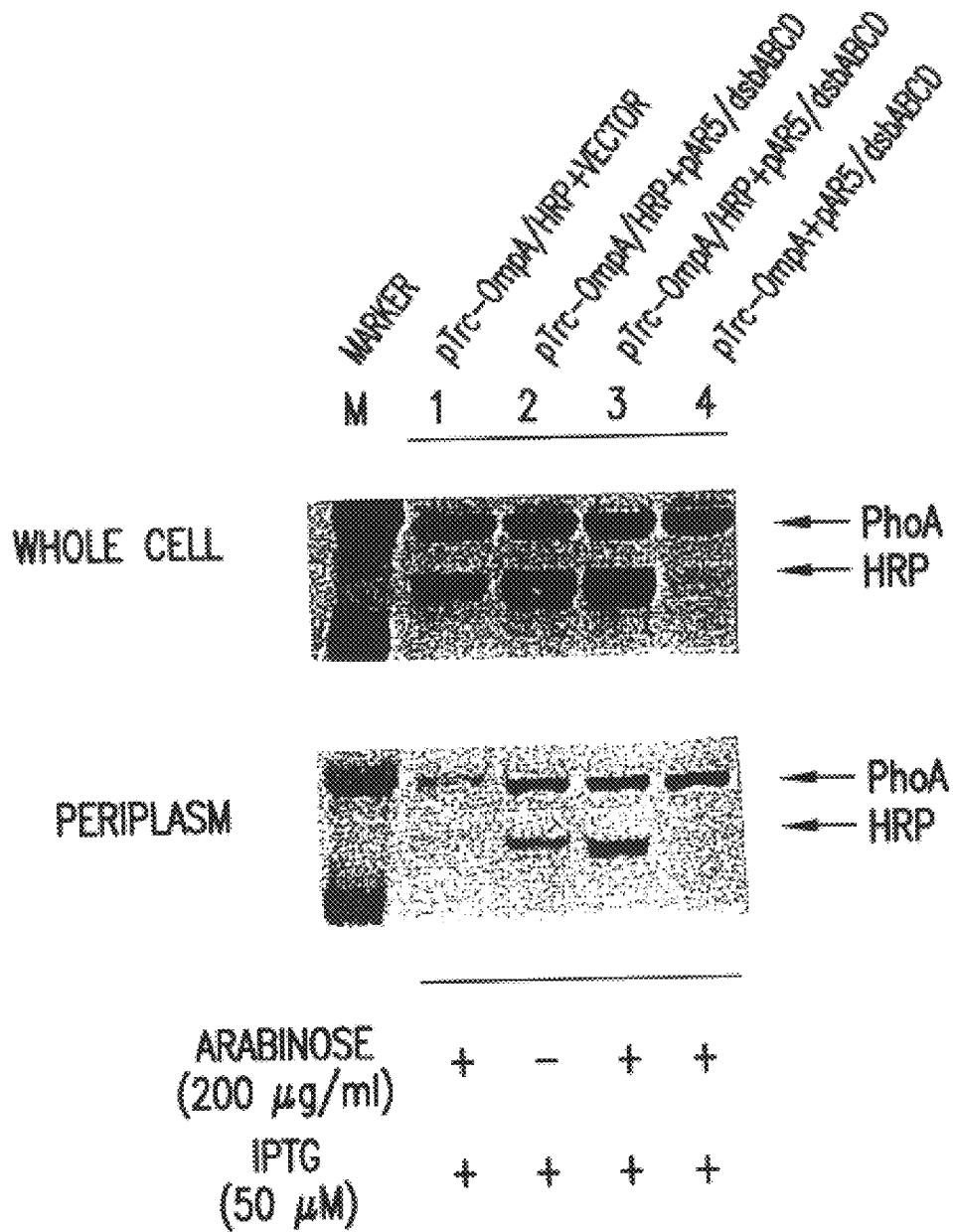
FIG. 7 shows changes in a total expression level of HRP or in a product level accumulated in each fraction, with respect to the change in the arabinose concentration.

Also, as shown in FIG. 7, when pTrc-OmpA/HRP and pAR5/dsbABCD were coexistent, the expression level of OmpA-HRP in the whole cell was about 2 to 3 times that of the case where pTrc-OmpA/HRP and vector pAR3 without inserts were coexistent. When pTrc-OmpA/HRP and pAR5/dsbABCD were coexistent, the expression level of OmpA-HRP in the periplasm soluble fraction was also increased in accordance with the arabinose concentration.

Example 8

Figure 8:
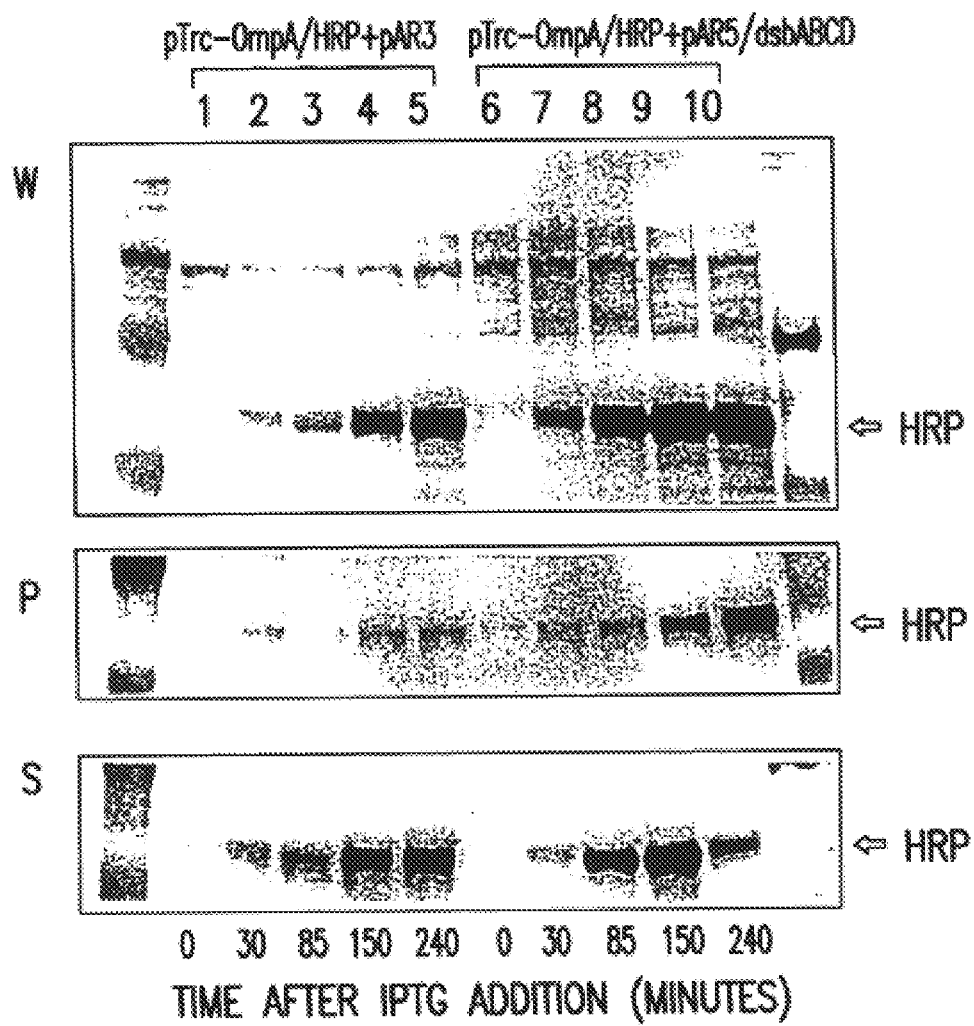
FIG. 8 shows the changes of the OmpA-HRP levels after 0, 30, 85, 150 and 240 minutes from the addition of IPTG and the localization (W: whole cell; P: periplasm soluble fraction; and S: spheroplast fraction)
Figure 9:
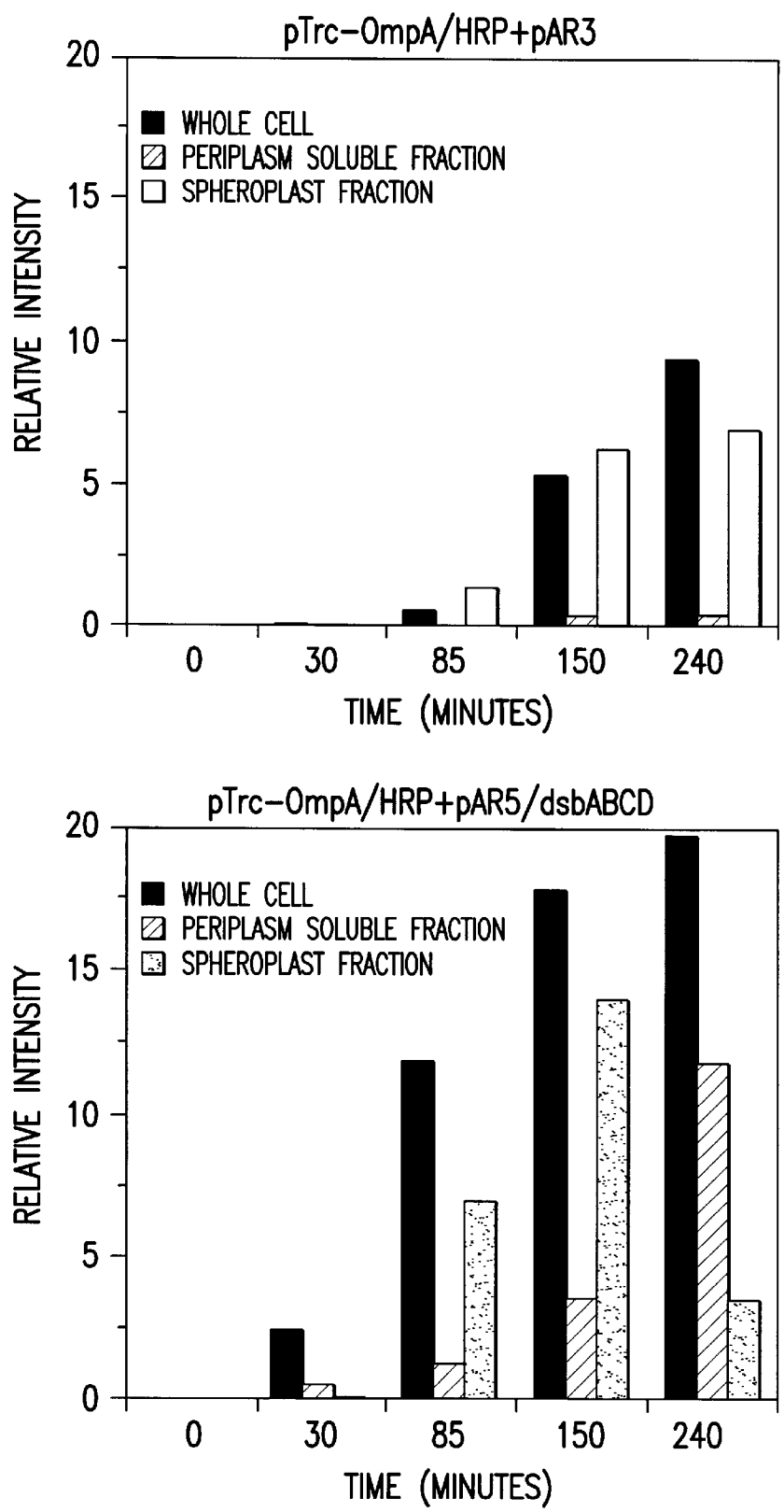
FIG. 9 is a set of graphs showing the relative expression levels of OmpA-HRP as determined from the results in FIG. 8, wherein the upper drawing is a graph showing the results of the control, and the lower drawing is a graph showing the results of pAR5/dsbABCD.

Changes in Expression Level and Localization of HRP Product in Prolonged Induction In order to examine the time course of the expression level and localization of the expression products, Omp-HRP and DsbABCD were induced and coexpressed by adding IPTG in the same manner as in Example 6 in the coexistence of pTrc-OmpA/HRP and pAR5/dsbABCD. As the control, the expression system in which pTrc-OmpA/HRP and vector pAR3 without inserts were coexistent was used. After adding IPTG, the culture was sampled at 0, 30, 85, 150, and 240 minutes thereafter in order to examine the changes in the expression level and the localization (the whole cell, the periplasm soluble fraction, or the spheroplast fraction) of OmpA-HRP contained in the culture. The whole cell and the periplasm soluble fraction were obtained in the same manner as in Examples 3 and 7. In addition, the spheroplast fraction was obtained as a fraction remaining after extraction of the periplasm soluble fraction by the lysozyme method. A sample containing the whole cell, the periplasm soluble fraction or the spheroplast fraction, which corresponded to 60 μl of culture with Klett units 80, was subjected to SDS-PAGE analysis and Western blotting to determine a relative expression level of OmpA-HRP. The results are shown in FIGS. 8 and 9. In FIG. 8, W is whole cell; P is a periplasm soluble fraction; and S is a spheroplast fraction.

It is shown from the results in FIG. 8 that in the system where OmpA-HRP and DsbABCD are coexpressed, the accumulation of OmpA-HRP is initiated about 30 minutes after adding IPTG, and thereafter reaches the maximum about 150 minutes after adding IPTG. In this expression level, HRP could be also confirmed by CBB staining. Also, it is shown in the results in FIG. 9 that the expression level of HRP in the periplasm soluble fraction, relative to the total amounts of HRP expressed, was about 10% after 85 minutes, but surprisingly increased up to about 60% after 240 minutes. By contrast, it is shown in the results in FIG. 9 that in the system in which pTrc-OmpA/HRP and vector pAR3 without inserts were coexistent, the accumulation of OmpA-HRP is at last initiated 150 minutes after adding IPTG (transition phase from the logarithmic growth phase to the stationary phase), and the accumulation thereof in the periplasm hardly occurs, showing accumulation of about 3% of whole expression level. Further, it is clear from the results in FIG. 6 that growth inhibition occurs along with expression of OmpA-HRP, whereby stopping the growth.

According to the present invention, there can be exhibited an excellent effect that a soluble expression product can be efficiently obtained because the formation of accurate disulfide bonds in the periplasm can be efficiently performed.

Equivalents

Those skilled in the art will recognize, or be able to ascertain using simple routine experimentation, many equivalents to the specific embodiments of the invention described in the present specification. Such equivalents are intended to be encompassed in the scope of the following claims.

What is claimed is:

1. An artificial operon comprising:
   (a) a polynucleotide comprising a nucleic acid sequence which encodes a polypeptide (DsbA) comprising an amino acid sequence set forth in SEQ ID NO:1, or
   (b) a polynucleotide comprising a nucleic acid sequence encoding DsbA that hybridizes under stringent conditions to the complement of SEQ ID NO:1,
      wherein the polypeptide encoded by the polynucleotide forms disulfide bonds in a nascent polypeptide chain which has been transferred into the periplasm;
   (c) a polynucleotide comprising a nucleic acid sequence which encodes a polypeptide (DsbB) comprising an amino acid sequence set forth in SEQ ID NO:3, or
   (d) a polynucleotide comprising a nucleic acid sequence encoding DsbB that hybridizes under stringent conditions to the complement of SEQ ID NO:3,
      wherein the polypeptide encoded by the polynucleotide reoxidizes DsbA;
   (e) a polynucleotide comprising a nucleic acid sequence which encodes a polypeptide (DsbC) comprising an amino acid sequence set forth in SEQ ID NO:5, or
   (f) a polynucleotide comprising a nucleic acid sequence encoding DsbC that hybridizes under stringent conditions to the complement of SEQ ID NO:5,
      wherein the polypeptide encoded by the polynucleotide corrects the disulfide by means of cleavage of the disulfide bonds followed by re-crosslinking; and
   (g) a polynucleotide comprising a nucleic acid sequence which encodes a polypeptide (DsbD) comprising an amino acid sequence set forth in SEQ ID NO:7, or
   (h) a polynucleotide comprising a nucleic acid sequence encoding DsbD that hybridizes under stringent conditions to the complement of SEQ ID NO:7,
      wherein the polypeptide encoded by the polynucleotide reduces DsbC.

2. The artificial operon according to claim 1, further comprising an inducible promoter, said promoter capable of expressing each of DsbA, DsbB, DsbC, and DsbD.

3. The artificial operon according to claim 2, wherein said inducible promoter is selected from the group consisting of lac, tac, trc, trp, ara, Pzt-1 and T7.

4. An artificial operon comprising a polynucleotide encoding DsbC and a polynucleotide encoding DsbD, wherein the polynucleotide encoding DsbC is selected from the group consisting of (e) a polynucleotide comprising a nucleic acid sequence which encodes a polypeptide comprising an amino acid sequence of SEQ ID NO: 5 (DsbC), or
   (f) a polynucleotide comprising a nucleic acid sequence that specifically hybridizes under stringent conditions to the complement of (e),
      wherein the polypeptide encoded by the polynucleotide corrects the disulfide by means of cleavage of the disulfide bonds followed by re-crosslinking; and the polynucleotide encoding DsbD is selected from the group consisting of
   (g) a polynucleotide comprising a nucleotide sequence which encodes a polypeptide comprising an amino acid sequence of SEQ ID NO:7 (DsbD), or
   (h) a polynucleotide comprising a nucleic acid sequence that specifically hybridizes to the complement of (g),
      wherein the polypeptide encoded by the polynucleotide re-reduces DsbC.

5. An expression plasmid comprising the artificial operon according to any one of claims 1, 2, 4.

6. A cotransformant obtainable by introducing both the expression plasmid according to claim 5 and an expression vector comprising a polynucleotide encoding a foreign protein into a host cell.

7. The cotransformant according to claim 6, wherein the host cell is an *E. coli* host cell.

8. The cotransformant according to claim 7, wherein the *E. coli* host cell is an *E. coli* protease mutant.

9. The cotransformant according to claim 7, wherein said foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotropic factors, brain-derived neurotrophic factors, glia cell line-derived neurotrophic factors, neurotrophin, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, leptin, immunoglobulins, single-chain antibodies, complement components, serum albumin, cedar pollen allergens, hypoxia-induced stress proteins, protein kinases, proto-oncogene products, transcription factors and virus-constitutive proteins.

10. The cotransformant according to claim 6, wherein said foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotropic factors, brain-derived neurotrophic factors, glia cell line-derived neurotrophic factors, neurotrophin, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, leptin, immunoglobulins, single-chain antibodies, complement components, serum albumin, cedar pollen allergens, hypoxia-induced stress proteins, protein kinases, proto-oncogene products, transcription factors and virus-constitutive proteins.

11. A method for producing a foreign protein in a host cell, comprising the steps of:
   culturing the cotransformant according to claim 6 under suitable conditions so as to cause expression of DsbA, DsbB, DsbC and DsbD, and the foreign protein; and
   purifying the foreign protein from the host cell.

12. The method according to claim 11, wherein the suitable conditions are those that cause expression of DsbA, DsbB, DsbC and DsbD at levels wherein the foreign protein is in a solubilized form.

13. The expression plasmid according to claim 5, further comprising a polynucleotide encoding a foreign protein operably linked to a promoter.

14. A transformant obtainable by introducing the expression plasmid according to claim 13 into a host cell.

* * * * *

SEQUENCE LISTING

```
<160> NUMBER OF SEQ ID NOS: 25

<210> SEQ ID NO 1
<211> LENGTH: 208
<212> TYPE: PRT
<213> ORGANISM: Escherichia coli

<400> SEQUENCE: 1

Met Lys Lys Ile Trp Leu Ala Leu Ala Gly Leu Val Leu Ala Phe
                 5                  10                  15

Ser Ala Ser Ala Ala Gln Tyr Glu Asp Gly Lys Gln Tyr Thr Thr
                20                  25                  30

Leu Glu Lys Pro Val Ala Gly Ala Pro Gln Val Leu Glu Phe Phe
                35                  40                  45

Ser Phe Phe Cys Pro His Cys Tyr Gln Phe Glu Glu Val Leu His
                50                  55                  60

Ile Ser Asp Asn Val Lys Lys Lys Leu Pro Glu Gly Val Lys Met
                65                  70                  75

Thr Lys Tyr His Val Asn Phe Met Gly Gly Asp Leu Gly Lys Glu
                80                  85                  90

Leu Thr Gln Ala Trp Ala Val Ala Met Ala Leu Gly Val Glu Asp
                95                 100                 105

Lys Val Thr Val Pro Leu Phe Glu Gly Val Gln Lys Thr Gln Thr
               110                 115                 120

Ile Arg Ser Ala Ser Asp Ile Arg Asp Val Phe Ile Asn Ala Gly
               125                 130                 135

Ile Lys Gly Glu Glu Tyr Asp Ala Ala Trp Asn Ser Phe Val Val
               140                 145                 150

Lys Ser Leu Val Ala Gln Gln Glu Lys Ala Ala Ala Asp Val Gln
               155                 160                 165

Leu Arg Gly Val Pro Ala Met Phe Val Asn Gly Lys Tyr Gln Leu
               170                 175                 180

Asn Pro Gln Gly Met Asp Thr Ser Asn Met Asp Val Phe Val Gln
               185                 190                 195

Gln Tyr Ala Asp Thr Val Lys Tyr Leu Ser Glu Lys Lys
               200                 205

<210> SEQ ID NO 2
<211> LENGTH: 647
<212> TYPE: DNA
<213> ORGANISM: Escherichia coli
```

-continued

<400> SEQUENCE: 2

```
atcggagaga gtagatcatg aaaaagattt ggctggcgct ggctggttta gttttagcgt      60
ttagcgcatc ggcggcgcag tatgaagatg gtaaacagta cactaccctg gaaaaaccag     120
ttgctggcgc gccgcaagtg ctggagtttt tctctttctt ctgcccgcac tgctatcagt     180
ttgaagaagt tctgcatatt tctgataacg tgaagaaaaa actgccggaa ggcgtgaaga     240
tgactaaaata ccacgtcaac ttcatggggg gtgacctggg caaagagctg actcaggcat     300
gggctgtggc gatggcgctg gcgtggaag acaaagtcac agttccgctg tttgaaggcg     360
tacaaaaaac ccagaccatt cgttcagcat ctgatatccg cgatgtattt atcaacgcag     420
gtattaaagg tgaagagtac gacgcggcgt ggaacagctt cgtggtgaaa tctctggtcg     480
ctcagcagga aaaagctgca gctgacgtgc aattgcgtgg tgttccggcg atgtttgtta     540
acggtaaata tcagctgaat ccgcagggta tggataccag caatatggat gttttttgttc     600
agcagtatgc tgatactgtg aaatatctgt ccgagaaaaa ataataa                    647
```

<210> SEQ ID NO 3
<211> LENGTH: 176
<212> TYPE: PRT
<213> ORGANISM: Escherichia coli

<400> SEQUENCE: 3

```
Met Leu Arg Phe Leu Asn Gln Cys Ser Gln Gly Arg Gly Ala Trp
                5                  10                  15
Leu Leu Met Ala Phe Thr Ala Leu Ala Leu Glu Leu Thr Ala Leu
               20                  25                  30
Trp Phe Gln His Val Met Leu Leu Lys Pro Cys Val Leu Cys Ile
               35                  40                  45
Tyr Glu Arg Cys Ala Leu Phe Gly Val Leu Gly Ala Ala Leu Ile
               50                  55                  60
Gly Ala Ile Ala Pro Lys Thr Pro Leu Arg Tyr Val Ala Met Val
               65                  70                  75
Ile Trp Leu Tyr Ser Ala Phe Arg Gly Val Gln Leu Thr Tyr Glu
               80                  85                  90
His Thr Met Leu Gln Leu Tyr Pro Ser Pro Phe Ala Thr Cys Asp
               95                 100                 105
Phe Met Val Arg Phe Pro Glu Trp Leu Pro Leu Asp Lys Trp Val
              110                 115                 120
Pro Gln Val Phe Val Ala Ser Gly Asp Cys Ala Glu Arg Gln Trp
              125                 130                 135
Asp Phe Leu Gly Leu Glu Met Pro Gln Trp Leu Leu Gly Ile Phe
              140                 145                 150
Ile Ala Tyr Leu Ile Val Ala Val Leu Val Ile Ser Gln Pro
              155                 160                 165
Phe Lys Ala Lys Lys Arg Asp Leu Phe Gly Arg
              170                 175
```

<210> SEQ ID NO 4
<211> LENGTH: 568
<212> TYPE: DNA
<213> ORGANISM: Escherichia coli

<400> SEQUENCE: 4

```
ctgcgcactc tatgcatatt gcagggaaat gattatgttg cgattttttga accaatgttc      60
```

-continued

```
acaaggccgg ggcgcgtggc tgttgatggc gtttactgct ctggcactgg aactgacggc    120
gctgtggttc cagcatgtga tgttactgaa accttgcgtg ctctgtattt atgaacgctg    180
cgcgttattc ggcgttctgg gtgctgcgct gattggcgcg atcgcccga  aaactccgct    240 gcgttatgta gcgatggtta tctggttgta tagtgcgttc cgcggtgtgc agttaactta    300
cgagcacacc atgcttcagc tctatccttc gccgtttgcc acctgtgatt ttatggttcg    360
tttcccggaa tggctgccgc tggataagtg ggtgccgcaa gtgtttgtcg cctctggcga    420
ttgcgccgag cgtcagtggg attttttagg tctggaaatg ccgcagtggc tgctcggtat    480
ttttatcgct tacctgattg tcgcagtgct ggtggtgatt tcccagccgt ttaaagcgaa    540
aaaacgtgat ctgttcggtc gctaataa                                       568
```

<210> SEQ ID NO 5
<211> LENGTH: 236
<212> TYPE: PRT
<213> ORGANISM: Escherichia coli

<400> SEQUENCE: 5

```
Met Lys Lys Gly Phe Met Leu Phe Thr Leu Leu Ala Ala Phe Ser
              5                   10                  15

Gly Phe Ala Gln Ala Asp Asp Ala Ala Ile Gln Gln Thr Leu Ala
             20                   25                  30

Lys Met Gly Ile Lys Ser Ser Asp Ile Gln Pro Ala Pro Val Ala
             35                   40                  45

Gly Met Lys Thr Val Leu Thr Asn Ser Gly Val Leu Tyr Ile Thr
             50                   55                  60

Asp Asp Gly Lys His Ile Ile Gln Gly Pro Met Tyr Asp Val Ser
             65                   70                  75

Gly Thr Ala Pro Val Asn Val Thr Asn Lys Met Leu Leu Lys Gln
             80                   85                  90

Leu Asn Ala Leu Glu Lys Glu Met Ile Val Tyr Lys Ala Pro Gln
             95                  100                 105

Glu Lys His Val Ile Thr Val Phe Thr Asp Ile Thr Cys Gly Tyr
            110                  115                 120

Cys His Lys Leu His Glu Gln Met Ala Asp Tyr Asn Ala Leu Gly
            125                  130                 135

Ile Thr Val Arg Tyr Leu Ala Phe Pro Arg Gln Gly Leu Asp Ser
            140                  145                 150

Asp Ala Glu Lys Glu Met Lys Ala Ile Trp Cys Ala Lys Asp Lys
            155                  160                 165

Asn Lys Ala Phe Asp Asp Val Met Ala Gly Lys Ser Val Ala Pro
            170                  175                 180

Ala Ser Cys Asp Val Asp Ile Ala Asp His Tyr Ala Leu Gly Val
            185                  190                 195

Gln Leu Gly Val Ser Gly Thr Pro Ala Val Val Leu Ser Asn Gly
            200                  205                 210

Thr Leu Val Pro Gly Tyr Gln Pro Pro Lys Glu Met Lys Glu Phe
            215                  220                 225

Leu Asp Glu His Gln Lys Met Thr Ser Gly Lys
            230                  235
```

<210> SEQ ID NO 6
<211> LENGTH: 720
<212> TYPE: DNA

<213> ORGANISM: Escherichia coli

<400> SEQUENCE: 6

```
ggaagattta tgaagaaagg ttttatgttg tttactttgt tagcggcgtt ttcaggcttt      60
gctcaggctg atgacgcggc aattcaacaa acgttagcca aaatgggcat caaaagcagc     120
gatattcagc ccgcgcctgt agctggcatg aagacagttc tgactaacag cggcgtgttg     180
tacatcaccg atgatggtaa acatatcatt caggggccaa tgtatgacgt tagtggcacg     240
gctccggtca atgtcaccaa taagatgctg ttaaagcagt tgaatgcgct tgaaaaagag     300
atgatcgttt ataaagcgcc gcaggaaaaa cacgtcatca ccgtgtttac tgatattacc     360
tgtggttact gccacaaact gcatgagcaa atggcagact acaacgcgct ggggatcacc     420
gtgcgttatc ttgctttccc cgcgccagggg ctggacagcg atgcagagaa agaaatgaaa    480
gctatctggt gtgcgaaaga taaaaacaaa gcgtttgatg atgtgatggc aggtaaaagc     540
gtcgcaccag ccagttgcga cgtggatatt gccgaccatt acgcacttgg cgtccagctt     600
ggcgttagcg gtactccggc agttgtgctg agcaatggca cacttgttcc gggttaccag     660
ccgaaagaga tgaaagaatt cctcgacgaa caccaaaaaa tgaccagcgg taaataataa     720
```

<210> SEQ ID NO 7
<211> LENGTH: 489
<212> TYPE: PRT
<213> ORGANISM: Escherichia coli

<400> SEQUENCE: 7

```
Met Gln Leu Pro Gln Gly Val Trp His Glu Asp Glu Phe Tyr Gly
                 5                  10                  15
Lys Ser Glu Ile Tyr Arg Asp Arg Leu Thr Leu Pro Val Thr Ile
                20                  25                  30
Asn Gln Ala Ser Ala Gly Ala Thr Leu Thr Val Thr Tyr Gln Gly
                35                  40                  45
Cys Ala Asp Ala Gly Phe Cys Tyr Pro Pro Glu Thr Lys Thr Val
                50                  55                  60
Pro Leu Ser Glu Val Val Ala Asn Asn Ala Ala Pro Gln Pro Val
                65                  70                  75
Ser Val Pro Gln Gln Glu Gln Pro Thr Ala Gln Leu Pro Phe Ser
                80                  85                  90
Ala Leu Trp Ala Leu Leu Ile Gly Ile Gly Ile Ala Phe Thr Pro
                95                 100                 105
Cys Val Leu Pro Met Tyr Pro Leu Ile Ser Gly Ile Val Leu Gly
               110                 115                 120
Gly Lys Gln Arg Leu Ser Thr Ala Arg Ala Leu Leu Leu Thr Phe
               125                 130                 135
Ile Tyr Val Gln Gly Met Ala Leu Thr Tyr Thr Ala Leu Gly Leu
               140                 145                 150
Val Val Ala Ala Ala Gly Leu Gln Phe Gln Ala Ala Leu Gln His
               155                 160                 165
Pro Tyr Val Leu Ile Gly Leu Ala Ile Val Phe Thr Leu Leu Ala
               170                 175                 180
Met Ser Met Phe Gly Leu Phe Thr Leu Gln Leu Pro Ser Ser Leu
               185                 190                 195
Gln Thr Arg Leu Thr Leu Met Ser Asn Arg Gln Gln Gly Gly Ser
               200                 205                 210
```

Pro Gly Gly Val Phe Val Met Gly Ala Ile Ala Gly Leu Ile Cys
            215                 220                 225

Ser Pro Cys Thr Thr Ala Pro Leu Ser Ala Ile Leu Leu Tyr Ile
            230                 235                 240

Ala Gln Ser Gly Asn Met Trp Leu Gly Gly Thr Leu Tyr Leu
            245                 250                 255

Tyr Ala Leu Gly Met Gly Leu Pro Leu Met Leu Ile Thr Val Phe
            260                 265                 270

Gly Asn Arg Leu Leu Pro Lys Ser Gly Pro Trp Met Glu Gln Val
            275                 280                 285

Lys Thr Ala Phe Gly Phe Val Ile Leu Ala Leu Pro Val Phe Leu
            290                 295                 300

Leu Glu Arg Val Ile Gly Asp Val Trp Gly Leu Arg Leu Trp Ser
            305                 310                 315

Ala Leu Gly Val Ala Phe Phe Gly Trp Ala Phe Ile Thr Ser Leu
            320                 325                 330

Gln Ala Lys Arg Gly Trp Met Arg Ile Val Gln Ile Ile Leu Leu
            335                 340                 345

Ala Ala Ala Leu Val Ser Val Arg Pro Leu Gln Asp Trp Ala Phe
            350                 355                 360

Gly Ala Thr His Thr Ala Gln Thr Gln Thr His Leu Asn Phe Thr
            365                 370                 375

Gln Ile Lys Thr Val Asp Glu Leu Asn Gln Ala Leu Val Glu Ala
            380                 385                 390

Lys Gly Lys Pro Val Met Leu Asp Leu Tyr Ala Asp Trp Cys Val
            395                 400                 405

Ala Cys Lys Glu Phe Glu Lys Tyr Thr Phe Ser Asp Pro Gln Val
            410                 415                 420

Gln Lys Ala Leu Ala Asp Thr Val Leu Leu Gln Ala Asn Val Thr
            425                 430                 435

Ala Asn Asp Ala Gln Asp Val Ala Leu Leu Lys His Leu Asn Val
            440                 445                 450

Leu Gly Leu Pro Thr Ile Leu Phe Phe Asp Gly Gln Gly Gln Glu
            455                 460                 465

His Pro Gln Ala Arg Val Thr Gly Phe Met Asp Ala Glu Thr Phe
            470                 475                 480

Ser Ala His Leu Arg Asp Arg Gln Pro
            485

<210> SEQ ID NO 8
<211> LENGTH: 1474
<212> TYPE: DNA
<213> ORGANISM: Escherichia coli

<400> SEQUENCE: 8
cgtgcagctg ccgcaaggcg tctggcatga agatgagttt acggcaaaa gcgagattta     60 ccgcgatcgg ctgacgcttc ccgtcaccat caaccaggcg agtgcgggag cgacgttaac    120
tgtcacctac cagggctgtg ctgatgccgg tttctgttat ccgccagaaa ccaaaaccgt    180
tccgttaagc gaagtggtcg ccaacaacgc agcgccacag cctgtgtctg ttccgcagca    240
agagcagccc accgcgcaat gccctttttc cgcgctctgg gcgttgttga tcggtattgg    300
tatcgccttt acgccatgcg tgctgccaat gtacccactg atttctggca tcgtgctggg    360
tggtaaacag cggctctcca ctgccagagc attgttgctg acctttattt atgtgcaggg    420

-continued

```
gatggcgctg acctacacgg cgctgggtct ggtggttgcc gccgcagggt tacagttcca    480
ggcggcgcta cagcacccat acgtgctcat tggcctcgcc atcgtcttta ccttgctggc    540
gatgtcaatg tttggcttgt ttaccctgca actccctct tcgctgcaaa cacgtctcac    600
gttgatgagc aatcgccaac agggcggctc acctggcggt gtgtttgtta tggggcgat    660 tgccggactg atctgttcac catgcaccac cgcaccgctt agcgcgattc tgctgtatat    720
cgcccaaagc gggaacatgt ggctgggcgg cggcacgctt tatctctatg cgttgggcat    780
gggcctgccg ctgatgctaa ttaccgtctt tggtaaccgc ttgctgccga aaagcggccc    840
gtggatggaa caagtcaaaa ccgcgtttgg ttttgtgatc ctcgcactgc cggtcttcct    900
gctggagcga gtgattggtg atgtatgggg attacgcttg tggtcggcgc tgggtgtcgc    960
attctttggc tgggcctttta tcaccagcct acaggctaaa cgcggctgga tgcgtattgt   1020
gcaaattatt ctgctggcag cggcattggt tagcgtgcgc ccacttcagg attgggcatt   1080
tggtgcgacg cataccgcgc aaactcagac gcatctcaac tttacacaaa tcaaaacggt   1140
agatgagtta aatcaggcgc tcgttgaagc caaaggcaaa ccggtgatgt tagatcttta   1200
tgccgactgg tgcgtcgcct gtaaagagtt tgagaaatac accttcagcg acccgcaggt   1260
gcaaaaagcg ttagcagaca cggtcttact tcaggccaac gtcacggcca acgacgcaca   1320
agatgtggcg ctgttaaagc atcttaatgt ccttggccta ccgacaattc tcttttttga   1380
cggacaaggc caggagcatc cacaagcacg cgtcacgggc tttatggatg ctgaaacctt   1440
cagcgcacat ttgcgcgatc gccaaccgtg ataa                                1474

<210> SEQ ID NO 9
<211> LENGTH: 23
<212> TYPE: DNA
<213> ORGANISM: Artificial Sequence

<400> SEQUENCE: 9
cggagctcat cggagagagt aga                                              23

<210> SEQ ID NO 10
<211> LENGTH: 28
<212> TYPE: DNA
<213> ORGANISM: Artificial Sequence

<400> SEQUENCE: 10
ggcccgggaa ttattatttt ttctcgga                                         28

<210> SEQ ID NO 11
<211> LENGTH: 34
<212> TYPE: DNA
<213> ORGANISM: Artificial Sequence

<400> SEQUENCE: 11
ggcccgggct gcgcactcta tgcatattgc aggg                                  34

<210> SEQ ID NO 12
<211> LENGTH: 34
<212> TYPE: DNA
<213> ORGANISM: Artificial Sequence

<400> SEQUENCE: 12
ggcatatgga ttattagcga ccgaacagat cacg                                  34

<210> SEQ ID NO 13
<211> LENGTH: 32
```

```
<212> TYPE: DNA
<213> ORGANISM: Artificial Sequence

<400> SEQUENCE: 13
ggcatatgag gaggaagatt tatgaagaaa gg                                32

<210> SEQ ID NO 14
<211> LENGTH: 44
<212> TYPE: DNA
<213> ORGANISM: Artificial Sequence

<400> SEQUENCE: 14
ccgtcgacga ttattattta ccgctggtca tttttttggtg ttcg                  44

<210> SEQ ID NO 15
<211> LENGTH: 42
<212> TYPE: DNA
<213> ORGANISM: Artificial Sequence

<400> SEQUENCE: 15
ccgtcgacga ggccgacatg cagctgccgc aaggcgtctg gc                    42

<210> SEQ ID NO 16
<211> LENGTH: 30
<212> TYPE: DNA
<213> ORGANISM: Artificial Sequence

<400> SEQUENCE: 16
ccgcatgctt atcacggttg gcgatcgcgc                                  30

<210> SEQ ID NO 17
<211> LENGTH: 3457
<212> TYPE: DNA
<213> ORGANISM: Artificial Sequence

<400> SEQUENCE: 17
gagctcatcg gagagagtag atcatgaaaa agatttggct ggcgctggct ggtttagttt      60
tagcgtttag cgcatcggcg gcgcagtatg aagatggtaa acagtacact accctggaaa     120
aaccagttgc tggcgcgccg caagtgctgg agttttttctc tttcttctgc ccgcactgct    180
atcagtttga agaagttctg catatttctg ataacgtgaa gaaaaaactg ccggaaggcg     240
tgaagatgac taaataccac gtcaacttca tggggggtga cctgggcaaa gagctgactc     300
aggcatgggc tgtggcgatg gcgctgggcg tggaagacaa agtcacagtt ccgctgtttg     360
aaggcgtaca aaaaacccag accattcgtt cagcatctga tatccgcgat gtatttatca     420
acgcaggtat taaaggtgaa gagtacgacg cggcgtggaa cagcttcgtg gtgaaatctc    480
tggtcgctca gcaggaaaaa gctgcagctg acgtgcaatt gcgtggtgtt ccggcgatgt    540
ttgttaacgg taaatatcag ctgaatccgc agggtatgga taccagcaat atggatgttt    600 tgttcagca gtatgctgat actgtgaaat atctgtccga gaaaaaataa taattcccgg     660
gctgcgcact ctatgcatat tgcagggaaa tgattatgtt gcgatttttg aaccaatgtt    720
cacaaggccg gggcgcgtgg ctgttgatgg cgtttactgc tctggcactg gaactgacgg    780
cgctgtggtt ccagcatgtg atgttactga aaccttgcgt gctctgtatt tatgaacgct    840
gcgcgttatt cggcgttctg ggtgctgcgc tgattggcgc gatcgccccg aaaactccgc    900
tgcgttatgt agcgatggtt atctggttgt atagtgcgtt ccgcggtgtg cagttaactt    960
acgagcacac catgcttcag ctctatcctt cgccgtttgc cacctgtgat tttatggttc   1020
```

```
gtttcccgga atggctgccg ctggataagt gggtgccgca agtgtttgtc gcctctggcg    1080
attgcgccga gcgtcagtgg gattttttag gtctggaaat gccgcagtgg ctgctcggta    1140
tttttatcgc ttacctgatt gtcgcagtgc tggtggtgat ttcccagccg tttaaagcga    1200
aaaaacgtga tctgttcggt cgctaataat ccatatgagg aggaagattt atgaagaaag    1260
gttttatgtt gtttactttg ttagcggcgt tttcaggctt tgctcaggct gatgacgcgg    1320
caattcaaca aacgttagcc aaaatgggca tcaaaagcag cgatattcag cccgcgcctg    1380
tagctggcat gaagacagtt ctgactaaca gcggcgtgtt gtacatcacc gatgatggta    1440
aacatatcat tcaggggcca atgtatgacg ttagtggcac ggctccggtc aatgtcacca    1500
ataagatgct gttaaagcag ttgaatgcgc ttgaaaaaga gatgatcgtt tataaagcgc    1560
cgcaggaaaa acacgtcatc accgtgttta ctgatattac ctgtggttac tgccacaaac    1620
tgcatgagca aatggcagac tacaacgcgc tgggatcac cgtgcgttat cttgctttcc    1680
cgcgccaggg gctggacagc gatgcagaga aagaaatgaa agctatctgg tgtgcgaaag    1740
ataaaaacaa agcgtttgat gatgtgatgg caggtaaaag cgtcgcacca gccagttgcg    1800
acgtggatat tgccgaccat tacgcacttg gcgtccagct tggcgttagc ggtactccgg    1860
cagttgtgct gagcaatggc acacttgttc cgggttacca gccgaaagag atgaaagaat    1920
tcctcgacga acaccaaaaa atgaccagcg gtaaataata atcgtcgacg aggccgacat    1980
gcagctgccg caaggcgtct ggcatgaaga tgagttttac ggcaaaagcg agatttaccg    2040
cgatcggctg acgcttcccg tcaccatcaa ccaggcgagt gcgggagcga cgttaactgt     210
cacctaccag ggctgtgctg atgccggttt ctgttatccg ccagaaacca aaaccgttcc    2160
gttaagcgaa gtggtcgcca acaacgcagc gccacagcct gtgtctgttc cgcagcaaga    2220
gcagcccacc gcgcaattgc cttttccgc gctctgggcg ttgttgatcg gtattggtat    2280
cgcctttacg ccatgcgtgc tgccaatgta cccactgatt tctggcatcg tgctgggtgg    2340
taaacagcgg ctctccactg ccagagcatt gttgctgacc tttatttatg tgcaggggat    2400
ggcgctgacc tacacggcgc tggtctggt ggttgccgcc gcaggttac agttccaggc    2460
ggcgctacag cacccatacg tgctcattgg cctcgccatc gtctttacct tgctggcgat    2520
gtcaatgttt ggcttgttta ccctgcaact cccctcttcg ctgcaaacac gtctcacgtt    2580
gatgagcaat cgccaacagg gcggctcacc tggcggtgtg tttgttatgg gggcgattgc    2640
cggactgatc tgttcaccat gcaccaccgc accgcttagc gcgattctgc tgtatatcgc    2700
ccaaagcggg aacatgtggc tgggcggcgg cacgctttat ctctatgcgt tgggcatggg    2760
cctgccgctg atgctaatta ccgtctttgg taaccgcttg ctgccgaaaa gcggcccgtg    2820
gatggaacaa gtcaaaaccg cgtttggttt tgtgatcctc gcactgccgg tcttcctgct    2880
ggagcgagtg attggtgatg tatggggatt acgcttgtgg tcggcgctgg gtgtcgcatt    2940
ctttggctgg gcctttatca ccagcctaca ggctaaacgc ggctggatgc gtattgtgca    3000
aattattctg ctggcagcgg cattggttag cgtgcgccca cttcaggatt gggcatttgg    3060
tgcgacgcat accgcgcaaa ctcagacgca tctcaacttt acacaaatca aaacggtaga    3120
tgagttaaat caggcgctcg ttgaagccaa aggcaaaccg gtgatgttag atctttatgc    3180
cgactggtgc gtcgcctgta aagagtttga gaaatacacc ttcagcgacc cgcaggtgca    3240
aaaagcgtta gcagacacgg tcttacttca ggccaacgtc acggccaacg acgcacaaga    3300
tgtgcgcgctg ttaaagcatc ttaatgtcct tggcctaccac aattctct tttttgacgg    3360
acaaggccag gagcatccac aagcacgcgt cacgggcttt atggatgctg aaaccttcag    3420
```
cgcacatttg cgcgatcgcc aaccgtgata agcatgc                                3457

<210> SEQ ID NO 18
<211> LENGTH: 64
<212> TYPE: DNA
<213> ORGANISM: Artificial Sequence
<220> FEATURE:
<223> OTHER INFORMATION: Duplex is formed in the region from position 5
      to 60 of the base sequence.
<400> SEQUENCE: 18
agctcgcgaa gcttgcatgc tgcagtcgac atatgcccgg gtaccgagct cgcggccgca    60
tgca                                                                  64

<210> SEQ ID NO 19
<211> LENGTH: 21
<212> TYPE: PRT
<213> ORGANISM: Artificial Sequence

<400> SEQUENCE: 19

Met Lys Lys Thr Ala Ile Ala Ile Ala Val Ala Leu Ala Gly Phe
 1               5                  10                  15

Ala Thr Val Ala Asn Ala
             20

<210> SEQ ID NO 20
<211> LENGTH: 73
<212> TYPE: DNA
<213> ORGANISM: Artificial Sequence

<400> SEQUENCE: 20
atgaaaaaga cagctatcgc gattgcagtg gcactggctg gtttcgctac cgtagcgcag    60
gccggctgaa ttc                                                        73

<210> SEQ ID NO 21
<211> LENGTH: 20
<212> TYPE: PRT
<213> ORGANISM: Artificial Sequence

<400> SEQUENCE: 21

Met Arg Ala Lys Leu Leu Gly Ile Val Leu Thr Thr Pro Ile Ala
 1               5                  10                  15

Ile Ser Ser Phe Ala
             20

<210> SEQ ID NO 22
<211> LENGTH: 70
<212> TYPE: DNA
<213> ORGANISM: Artificial Sequence

<400> SEQUENCE: 22
atgcgcgcga aactgctggg tattgtcctg acgaccccga tcgcgatcag ctcttttgcc    60
ggctgaattc                                                            70

<210> SEQ ID NO 23
<211> LENGTH: 36
<212> TYPE: DNA
<213> ORGANISM: Artificial Sequence

<400> SEQUENCE: 23
agcagctccc atccgatctt ccaccgcggc gaattc                               36

```
<210> SEQ ID NO 24
<211> LENGTH: 21
<212> TYPE: DNA
<213> ORGANISM: Artificial Sequence

<400> SEQUENCE: 24
atgcagttaa cccctacatt c                                                  21

<210> SEQ ID NO 25
<211> LENGTH: 21
<212> TYPE: DNA
<213> ORGANISM: Artificial Sequence

<400> SEQUENCE: 25
ggggaattcg gatccttatt a                                                  21
```